United States Patent
Hossack et al.

[11] Patent Number: 6,027,448
[45] Date of Patent: *Feb. 22, 2000

[54] ULTRASONIC TRANSDUCER AND METHOD FOR HARMONIC IMAGING

[75] Inventors: John A. Hossack, Palo Alto; Christopher R. Cole, Redwood City; Jian-Hua Mo, Milpitas, all of Calif.

[73] Assignee: Acuson Corporation, Mountain View, Calif.

[*] Notice: This patent is subject to a terminal disclaimer.

[21] Appl. No.: 09/103,320

[22] Filed: Jun. 23, 1998

Related U.S. Application Data

[63] Continuation-in-part of application No. 08/950,706, Oct. 15, 1997, which is a continuation of application No. 08/675,412, Jul. 2, 1996, Pat. No. 5,678,554, and a continuation-in-part of application No. 08/926,270, Sep. 5, 1997, which is a continuation of application No. 08/771,345, Dec. 16, 1996, Pat. No. 5,696,737, which is a continuation of application No. 08/397,833, Mar. 2, 1995, Pat. No. 5,608,690.

[51] Int. Cl.$^7$ ........................................................ A61B 8/00
[52] U.S. Cl. ........................................................ 600/447
[58] Field of Search ........................................ 600/443, 454, 600/458, 447, 459; 128/916; 367/711, 138

[56] References Cited

U.S. PATENT DOCUMENTS

| | | |
|---|---|---|
| 3,953,825 | 4/1976 | Kino et al. . |
| 4,016,750 | 4/1977 | Green . |
| 4,016,751 | 4/1977 | Kossoff . |
| 4,140,022 | 2/1979 | Maslak . |
| 4,350,917 | 9/1982 | Lizzi et al. . |
| 4,395,912 | 8/1983 | Hassler . |
| 4,403,311 | 9/1983 | Tournois . |
| 4,403,314 | 9/1983 | Tournois . |
| 4,425,525 | 1/1984 | Smith et al. . |
| 4,446,740 | 5/1984 | Wilson et al. . |
| 4,456,982 | 6/1984 | Tournois . |
| 4,458,342 | 7/1984 | Tournois . |

(List continued on next page.)

FOREIGN PATENT DOCUMENTS

| | | |
|---|---|---|
| 0 357 164 | 3/1990 | European Pat. Off. . |
| 0 770 352 A1 | 5/1997 | European Pat. Off. . |

OTHER PUBLICATIONS

Marc Gensane, "Bubble population measurements with a parametric array." J. Acoustical Society of America, 95 (6), Jun. 1994.

Ken Ishihara, et al., "New Approach to Noninvasive Manometry Based on Pressure Dependent Resonant Shift of Elastic Microcapsules in Ultrasonic Frequency Characteristics." Japanese J. of Applied Physics, vol. 2 (1988).

(List continued on next page.)

*Primary Examiner*—George Manuel
*Attorney, Agent, or Firm*—Brinks Hofer Gilson & Lione

[57] ABSTRACT

A method and system for ultrasonically imaging a target during an imaging session. The method includes the steps of transmitting ultrasonic energy at a fundamental frequency into the target from a plurality of transducer elements wherein each transducer element has a non-planar surface and shape that either focuses different frequency components at different focal points along a focal line or focuses common frequency components at different focal points along a focal line; and selectively receiving reflected ultrasonic echo information in the vicinity of a harmonic frequency while filtering out ultrasonic echo information at the fundamental frequency. The ultrasonic imaging system includes an ultrasonic transducer array comprising a plurality of transducer elements wherein each element has a non-planar surface in an elevation direction, and each transducer element has a shape that focuses different frequency components at different focal points along a focal line; transmit circuitry coupled to the transducer array, said transmit circuitry operative to transmit energy at a fundamental frequency; and receive circuitry coupled to the transducer array for selectively receiving ultrasonic echo information in the vicinity of a harmonic frequency from the target while filtering out ultrasonic echo information at the fundamental frequency.

43 Claims, 13 Drawing Sheets

U.S. PATENT DOCUMENTS

| | | |
|---|---|---|
| 4,460,841 | 7/1984 | Smith et al. . |
| 4,534,221 | 8/1985 | Fife et al. . |
| 4,550,607 | 11/1985 | Maslak et al. . |
| 4,699,009 | 10/1987 | Maslak et al. . |
| 4,712,037 | 12/1987 | Verbeek et al. . |
| 4,870,871 | 10/1989 | Russell et al. . |
| 4,974,558 | 12/1990 | Katakura et al. . |
| 5,014,712 | 5/1991 | O'Donnell . |
| 5,040,537 | 8/1991 | Katakura . |
| 5,105,814 | 4/1992 | Drukarey et al. . |
| 5,111,823 | 5/1992 | Cohen . |
| 5,113,706 | 5/1992 | Pittaro . |
| 5,115,809 | 5/1992 | Saitoh et al. . |
| 5,142,649 | 8/1992 | O'Donnell . |
| 5,190,766 | 3/1993 | Ishihara . |
| 5,195,520 | 3/1993 | Schlief et al. . |
| 5,215,680 | 6/1993 | D'Arrigo . |
| 5,218,869 | 6/1993 | Pummer . |
| 5,219,401 | 6/1993 | Cathignol et al. . |
| 5,228,007 | 7/1993 | Murakami et al. . |
| 5,235,982 | 8/1993 | O'Donnell . |
| 5,255,683 | 10/1993 | Monaghan . |
| 5,301,674 | 4/1994 | Erikson et al. . |
| 5,305,756 | 4/1994 | Entrekin et al. . |
| 5,322,068 | 6/1994 | Thiele et al. . |
| 5,358,466 | 10/1994 | Aida et al. . |
| 5,380,411 | 1/1995 | Schlief . |
| 5,410,205 | 4/1995 | Gururaja . |
| 5,410,516 | 4/1995 | Uhlendorf et al. . |
| 5,415,175 | 5/1995 | Hanafy et al. . |
| 5,417,214 | 5/1995 | Roberts et al. . |
| 5,417,219 | 5/1995 | Takamizawa et al. . |
| 5,425,366 | 6/1995 | Reinhardt et al. . |
| 5,433,207 | 7/1995 | Pretlow, III . |
| 5,438,554 | 8/1995 | Seyed-Bolorforosh et al. . |
| 5,438,998 | 8/1995 | Hanafy . |
| 5,456,255 | 10/1995 | Abe et al. . |
| 5,456,257 | 10/1995 | Johnson et al. . |
| 5,469,849 | 11/1995 | Sasaki et al. . |
| 5,479,926 | 1/1996 | Ustuner et al. . |
| 5,482,046 | 1/1996 | Deitrich . |
| 5,523,058 | 6/1996 | Umemura et al. . |
| 5,526,816 | 6/1996 | Arditi . |
| 5,546,946 | 8/1996 | Souquet . |
| 5,558,092 | 9/1996 | Unger et al. . |
| 5,560,364 | 10/1996 | Porter . |
| 5,565,628 | 10/1996 | Lorraine . |
| 5,577,505 | 11/1996 | Brock-Fisher et al. . |
| 5,579,768 | 12/1996 | Klesenski . |
| 5,579,770 | 12/1996 | Finger . |
| 5,580,575 | 12/1996 | Unger et al. . |
| 5,601,086 | 2/1997 | Pretlow, III et al. . |
| 5,617,862 | 4/1997 | Cole et al. . |
| 5,628,322 | 5/1997 | Mine . |
| 5,632,277 | 5/1997 | Chapman et al. . |
| 5,675,554 | 10/1997 | Cole . |
| 5,678,554 | 10/1997 | Hossack et al. . |
| 5,685,308 | 11/1997 | Wright et al. . |
| 5,696,737 | 12/1997 | Hossack et al. . |
| 5,724,976 | 3/1998 | Mine et al. . |
| 5,740,128 | 4/1998 | Hossack . |

OTHER PUBLICATIONS

V.L. Newhouse, et al., "Bubble size measurements using the nonlinear mixing of two frequencies." J. Acoustical Society of America, 75 (5), May 1984.

"Small Spheres Lead to Big Ideas." Research News, Science vol. 267, Jan. 20, 1995.

Abstracts Journal of the American Society of Echocardiography, vol. 8, No. 3 pp. 345–346, 355, 358–364.

Deborah J. Rubens, MD, et al., "Sonoelasticity Imaging of Prostate Cancer: In Vitro Results." Radiology, vol. 195, No. 2, 1995.

B. Schrope, et al., "Simulated Capillary Blood Flow Measurement Using a Nonlinear Ultrasonic Contrast Agent." Ultrasonic Imaging 14 (1992).

Fred Lee, Jr., MD, et al., "Sonoelasticity Imaging: Results in In Vitro Tissue Specimens." Radiology, vol. 181, No. 1 (1991).

Kevin J. Parker, PhD., et al., "Sonoelasticity of Organs: Shear Waves Ring A Bell." J. Ultrasound Med., 11 (1992).

William Armstrong, M.D., et al., "Position Paper on Contrast Echocardiography." American Society of Echocardiography, draft 1, Jun. 6, 1994.

K.J. Parker, et al., "Tissue Response to Mechanical Vibrations for 'Sonoelasticity Imaging'." Ultrasound in Med. and Biol., vol. 16, No. 3 (1990).

Robert M. Lerner, et al., "Sonoelasticity" Images Derived from Ultrasound Signals in Mechanically Vibrated Tissues., Ultrasound in Med. and Biol., vol. 16, No. 3 (1990).

Excerpt from Ultrasonics: Fundamentals and Applications (1992), pp. 380–393, 363–365.

J.A. Hossack, et al., "Improving Transducer Performance Using Multiple Active Layers." SPIE vol. 1733 (1992).

Volkmar Uhlendorf, et al., "Nonlinear Acoustical Response of Coated Microbubbles in Diagnostic Ultrasound." IEEE 1994 Ultrasonics Symposium.

John A. Hossack, et al., "Improving the Characteristics of a Transducer Using Multiple Piezoelectric Layers." IEEE Transactions on Ultrasonics, Ferroelectrics, and Frequency Control, vol. 40, No. 2, Mar. 1993.

H. Edward Karrer, et al., "A Phased Array Acoustic Imaging System for Medical Use." IEEE 1980 Ultrasonics Symposium.

1980 IEEE Ultrasonics Symposium, pp. 757–762.

Entrekin, R., et al., "Real–time 3–D Ultrasund Imaging With a 1–D"Fan Beam" Transducer Array," pp. 264–271, SPIE vol. 1733 (1992).

Devonald, K., et al., "Volume Imaging: Three–Dimensional Appreciation of the Fetal Head and Face," pp. 919–925, J. Ultrasound Med. (1995).

Tournois, P., "Acoustical Imaging Via Coherent Reception of Spatially Coloured Transmissions," Ultrasonics Symposium, pp. 747–750 (1980).

Hernandez, J. et al., Synthesis of the Driving Functions of an Array for Propagating Localized Wave Energy, J. Acoust. Soc. Am. 92(1), pp. 550–562, Jul. 1992.

Jian–Yu Lu et al., "Ultrasonic Nondiffracting Transducer for Medical Imaging," IEEE Transactions on Ultrasonics, Ferroelectrics, and Frequency Control, vol. 37, No. 5, Sep. 1990.

Jian–Yu Lu et al., IEEE Transactions on Ultrasonics, Ferroelectrics, and Frequency Control, vol. 39, No. 3, May 1992, "Experimental Verification of Nondiffracting X Waves," pp. 441–446.

Synchronous Dynamic Focusing for Ultrasound Imaging: G. Manes, et al.; IEEE Transactions on Ultrasonics, Ferroelectrics, and Frequency Control, vol. 35, No. 1, Jan. 1988; pp. 14–21.

Properties of Swept FM Waveforms in Medical Ultrasound Imaging; C.R. Cole; 1991 Ultrasonics Symposium, pp. 1243–1248.

Frequency Synthesis by Phase Lock; William F. Egan, Ph.D., Senior Engineering Specialist GTE Products Corporation; Lecturer in Electrical Engineering University of Santa Clara, Robert E. Krieger Publishing Company, Malabar, Florida 1990; pp. 14–29.

Stanford Research Systems; Synthesized Function Generator; Model DS345–30 MHz Function & Arbitrary Waveform Generator; 1994; pp. 8–13.

Stanford Research Systems; Scientific and Engineering Instruments 1994–1995; pp. 171–176.

IEEE Transactions on Ultrasonics, Ferroelectrics, and Frequency Control, vol. 39, No. 1, Jan. 1992, "Non–diffracting X Waves–Exact Solutions to Free–Space Scalar Wave Equation and Their Finite Aperture Realizations", Jian–Yu Lu et al., pp. 19–31.

J. Accoust. Soc. Am., vol. 89, No. 4, Pt. 1, Gordon Hayward et al., "A Thin Film Technique for Spatial Apodization of Disc–Shaped Piezoceramic Transducers"; Apr. 1991; pp. 1808–1815.

IEEE Transactions on Ultrasonics, Ferroelectrics, and Frequency Control, vol. 39, No. 3, Matthew O'Donnell, "Coded Excitation System for Improving the Penetration of Real–Time Phased–Array Imaging Systems"; May 1992; pp. 341–351.

Ultrasonics Symposium, Volkmar Uhlendorf et al., "Nonlinear Acoustical Response of Coated Microbubbles in Diagnostic Ultrasound," 1994; pp. 1559–1562.

6,027,448

ULTRASONIC TRANSDUCER AND METHOD FOR HARMONIC IMAGING

CROSS REFERENCE TO RELATED APPLICATION

This application is a continuation-in-part of U.S. patent application Ser. No. 08/950,706, filed Oct. 15, 1997 which is a continuation of U.S. Ser. No. 08/675,412 filed Jul. 2, 1996, now U.S. Pat. No. 5,678,554 issued Oct. 21, 1997 and also a continuation-in-part of U.S. Ser. No. 08/926,270 filed Sep. 5, 1997 which is a continuation of U.S. Ser. No. 08/771,345 filed Dec. 16, 1996, now U.S. Pat. No. 5,696,737 which is a continuation of U.S. patent application Ser. No. 08/397,833 filed Mar. 2, 1995, now U.S. Pat. No. 5,608,690 issued Mar. 4,1997, all of which are hereby specifically incorporated by reference.

BACKGROUND OF THE INVENTION

This invention relates to an ultrasound transducer and a method for harmonic imaging, and in particular, to an ultrasound transducer and method for focusing an ultrasound beam at multiple focal points and utilizing reflected ultrasonic energy at a harmonic of a transmitted fundamental frequency signal, for example, to image contrast agents or for tissue harmonic imaging when no contrast agent is used.

Contrast agents are described, for example, by V. Uhlendorf, et al., in "Nonlinear Acoustical Response of Coated Microbubbles in Diagnostic Ultrasound" (1995 Ultrasonic Symposium, pp.1559–1562). Such contrast agents possess a fundamental resonant frequency. When they are insonified with high intensity ultrasonic energy at this fundamental frequency, a strong non-linear response is caused which is stronger in the agent than in the tissue, i.e., they radiate ultrasonic frequency at a harmonic of the fundamental frequency. Such contrast agents are often used to highlight regions containing blood loaded with the contrast agent. For example, in the case of a blood-filled chamber of the heart, the borders of the chamber can be distinguished more easily when contrast agent is used. Since the contrast agent generates more harmonic ultrasound energy, than from tissue signals, signals from the tissue may be reduced by filtering out the fundamental response at the receive beamformer. In addition, it may be desirable to provide an ultrasonic system that is responsive to reflected harmonic signals even when a contrast agent is not injected into a target because tissue itself produces a non-linear response.

Typically, contrast imaging is performed with an imaging system having a transmit beamformer that transmits ultrasonic energy at a fundamental frequency and a receive beamformer responsive to a harmonic of the fundamental frequency. In order to image the contrast agent or tissue, if no contrast agent is used, clearly, it is known to reduce energy at the harmonic in the transmit beam, and to reduce sensitivity of the receive beamformer to energy at the fundamental frequency. In the past, this has been accomplished by using a burst of square or sine waves to form the transmit beam, and by using appropriate band pass or high pass filters in the receive beamformer. Though a large pulse count reduces energy at the harmonic, it reduces time resolution of the pulse, and therefore spatial resolution of the resulting image.

The present invention is directed to further improvements that enhance the collection of reflected ultrasonic energy at a harmonic of a transmitted signal.

SUMMARY OF THE INVENTION

According to a first aspect of the present invention there is provided a method for ultrasonically imaging a target during an imaging session, said method comprising the following steps:

(a) transmitting ultrasonic energy at a fundamental frequency into the target from a plurality of transducer elements wherein each transducer element has a non-planar surface and a shape that focuses different frequency components at different focal points along a focal line; and (b) selectively receiving ultrasonic echo information in the vicinity of a harmonic frequency from the target while filtering out ultrasonic echo information at the fundamental frequency.

According to a second aspect of the present invention there is provided an ultrasonic imaging system comprising:

an ultrasonic transducer array comprising a plurality of transducer elements wherein each element has a non-planar surface in an elevation direction, and each transducer has a shape that focuses different frequency components at different focal points along a focal line;

transmit circuitry coupled to the transducer array said transmit circuitry operative to transmit energy at a fundamental frequency; and receive circuitry coupled to the transducer array, said receive circuitry operative to selectively receive ultrasonic echo information in the vicinity of a harmonic frequency from the target while filtering out ultrasonic echo information at the fundamental frequency.

According to a third aspect of the present invention there is provided a method for ultrasonically imaging a target during an imaging session, said method comprising the steps of:

(a) transmitting ultrasonic energy at a fundamental frequency into the target by a transducer element wherein the transducer element has a shape that focuses different fundamental frequency components at different focal points; and (b) receiving ultrasonic echo information in the vicinity of a harmonic frequency from the target while filtering out ultrasonic echo information at the fundamental frequency;

(c) generating an image display from ultrasonic echo information at a harmonic frequency of the transmitted fundamental frequency.

According to a fourth aspect of the present invention there is provided a method for ultrasonically imaging a target during an imaging session, said method comprising the following steps:

(a) transmitting ultrasonic energy at a fundamental frequency into the target from a plurality of transducer elements wherein each transducer element has a non-planar surface and a shape that focuses different frequency components at common focal points along a focal line; and (b) selectively receiving ultrasonic echo information in the vicinity of a harmonic frequency from a target while filtering out ultrasonic echo information at the fundamental frequency.

According to a fifth aspect of the present invention there is provided an ultrasonic imaging system comprising:

an ultrasonic transducer array comprising a plurality of transducer elements wherein each element has a non-planar surface in an elevation direction, and each transducer has a shape that focuses different frequency components at common focal points along a focal line;

transmit circuitry coupled to the transducer array said transmit circuitry operative to transmit energy at a fundamental frequency; and receive circuitry coupled to the transducer array, said receive circuitry operative to receive ultrasonic echo information in the vicinity of a harmonic frequency from a target while filtering out ultrasonic echo information from the fundamental frequency.

According to a sixth aspect of the present invention there is provided a method for ultrasonically imaging a target during an imaging session, said method comprising the steps of:

(a) transmitting ultrasonic energy at a fundamental frequency into the target by a transducer array wherein the transducer array has a shape that focuses common fundamental frequency components at different focal points;

(b) selectively filtering out ultrasonic echo information at the transmitted fundamental frequency; and (c) generating an image display from the second harmonic echo information.

According to a seventh embodiment of the present invention there is provided an ultrasonic imaging system comprising:

an ultrasonic transducer array comprising a plurality of transducer elements, each of the transducer elements having a thickness that varies in the elevation direction from a first end to a second end of the transducer element, wherein the transducer element is thinnest at the first end and thickest at the second end;

transmit circuitry coupled to the transducer array, said transmit circuitry operative to transmit energy at a fundamental frequency; and receive circuitry coupled to the transducer array, said receive circuitry operative to selectively receive ultrasonic echo information in the vicinity of a harmonic frequency from the target while filtering out ultrasonic echo information at the fundamental frequency.

DETAILED DESCRIPTION OF THE PRESENTLY PREFERRED EMBODIMENTS

The preferred embodiments of the transducers described below are designed to focus an ultrasound beam at multiple focal points or along a line of focal points and collect harmonic energy in the beam reflected from a target in a simple manner.

Figure 1:
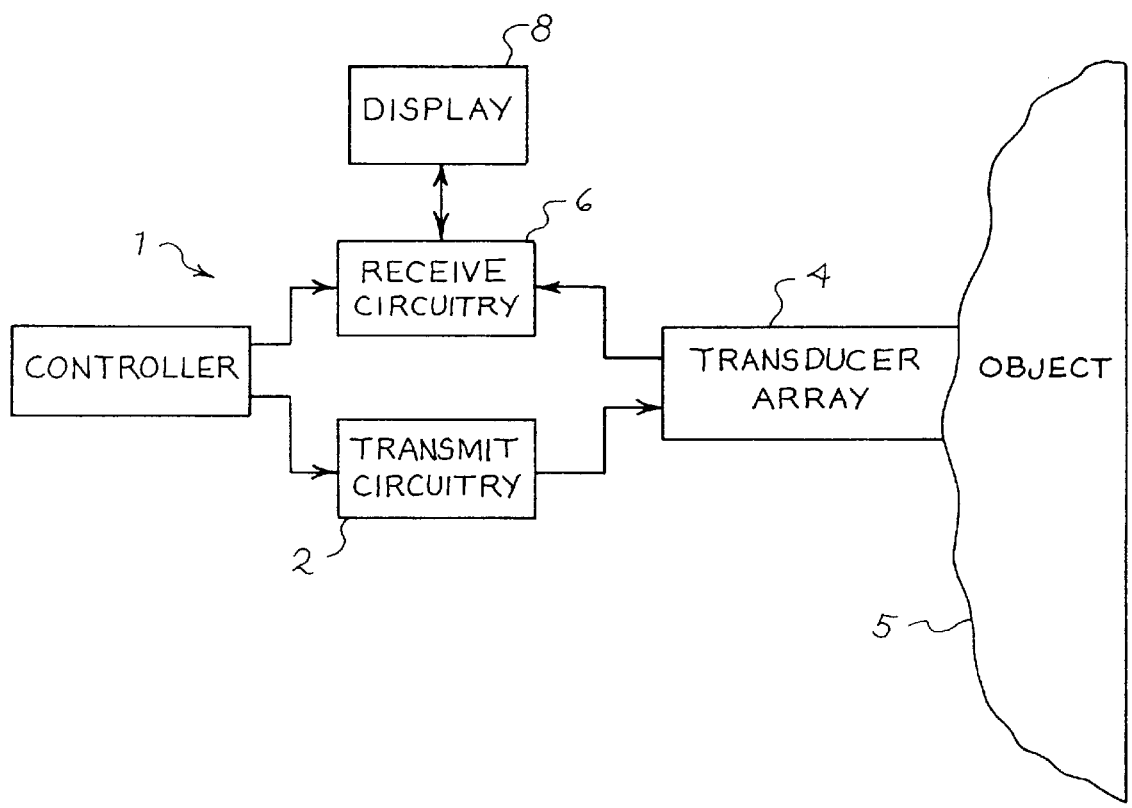
FIG. 1 is a block diagram of an ultrasound system for generating an image of a target being observed.

FIG. 1 is a block diagram of an ultrasound system 1 for generating an image of a target or body 5 being observed. The ultrasound system 1 has transmit circuitry 2 for transmitting electrical signals to a transducer assembly 4, receive circuitry 6 for processing the signals received by the transducer assembly 4, and a display 8 for providing the image of the object 5 being observed. Preferably, the transducer assembly 4 is hand-held and can be adjusted in position to direct the ultrasound beam to the region of interest. The transducer assembly 4 converts electrical signals provided by the transmit circuitry 2 to pressure waves and converts pressure waves reflected from the target 5 being observed to electrical signals which are then processed in the receive circuitry 6 and ultimately displayed on a display 8.

The transmit circuitry 2 includes a transmit beamformer preferably controlled by a controller 15 which applies analog transmit voltage waveforms via a multichannel switch (not shown) to an array 10 of transducer elements 11 housed in the assembly 4. (See FIG. 2). Various embodiments of transmit beamformers suitable for use in the system of FIG. 1 will be described hereinafter.

The receive circuitry 6 may filter the received signal to help optimize the beam forming process by selectively emphasizing those frequencies of most interest and rejecting those frequencies containing less useful signal and/or noise. As used herein, "frequency" is meant to encompass a signal having a finite bandwidth and is not intended to be limited to a single frequency. Suitable delays are also applied to the receive waveforms to create a coherent sum for selected points along the spatial axis.

In one mode of operation, the receive beamformer selects delays to focus an emitted ultrasound beam at progressively longer ranges along a line of focus, thereby sampling multiple points along the line. In order to take advantage of the time-varying frequency distribution of ultrasonic energy along the line of focus, the receive beamformer preferably includes a time-varying filter that attenuates frequency components of the receive waveforms other than those characteristic of the focal range of interest. The operation of the time-varying bandpass filter will be described in greater detail hereinafter.

Figure 2:
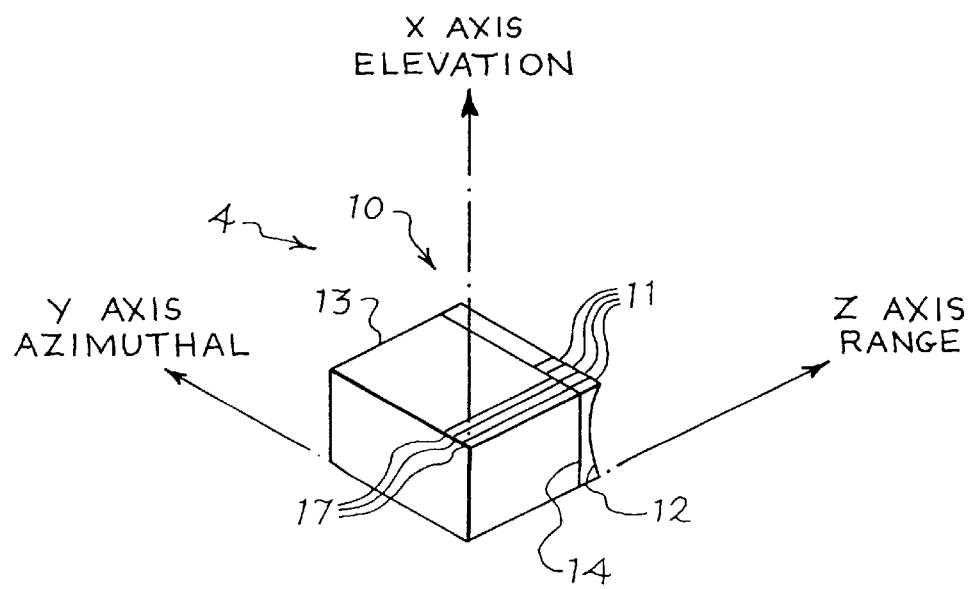
FIG. 2 is a perspective view of a portion of the transducer assembly shown in FIG. 1.

FIG. 2 is a perspective view of a portion of the transducer assembly 4 shown in FIG. 1. To simplify and illustrate the relevant features of the transducer assembly 4 not all of the components forming the assembly have been shown. Referring to FIG. 2, the assembly 4 contains an array 10 of transducer elements 11. Transducer element refers to a layer of transducer material such as a piezoelectric ceramic that generates pressure waves in response to an applied electric field. Adapted from radar terminology, the indicated x, y and z directions are referred togas the azimuth, elevation and range directions or axes, respectively. Typically, there are one hundred twenty eight transducer elements 11 sequentially disposed along the y-azimuth axis. The array may, however, consist of any number of transducer elements 11 each arranged in any desired geometrical configuration. Details concerning the construction of the transducer array 10 may be discerned from U.S. Pat. No. 5,678,554 previously referred to above.

Figure 3:
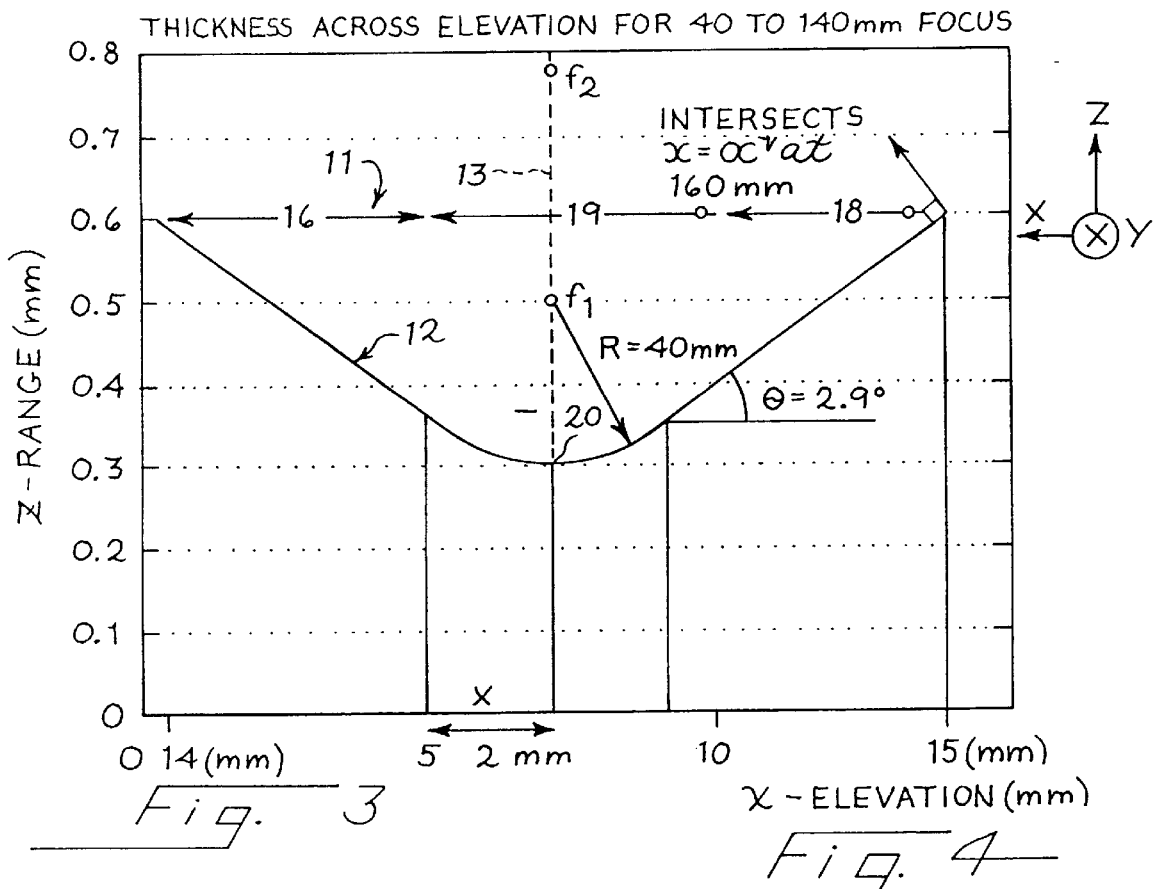
FIG. 3 is a graph illustrating the cross-sectional profile of a transducer element according to a first preferred embodiment of the present invention.

FIG. 3 is a graph illustrating the cross-sectional profile of a transducer element according to a first preferred embodiment of the present invention. The elevation direction is along the horizontal axis and the range direction is along the vertical axis. The units of division along both axes are in millimeters. Transducer element 11 has a front portion 12, a back portion 14, a center portion 19, and two side portions 16 and 18. The front portion 12 is the surface which is positioned to face the region of examination. The back portion 14 may be shaped as desired, but is generally a planar surface. Preferably the profile or surface geometry of the front portion 12 of the transducer element is a negatively "curved" surface with the thickness of the element 11 being greater at its side portions 16 and 18 than at its center portion 19. The thickness of the element 11 is defined along the range axis.

As was described in U.S. Pat. No. 5,678,554, the shape of the transducer element according to this preferred embodiment and the other preferred embodiments described hereinafter has a surface geometry that allows different frequencies of a transmitted ultrasound beam to be focused at different focal points. The focal point is defined by the intersection of a line perpendicular to the active surface of the transducer element and the axis 13 of the transducer. The surface geometry of the transducer element 11 shown in FIG. 3 has a center portion 19 defined by a circular arc and side portions 16 and 18 defined by straight segments. If only the center portion 19 of the transducer element is excited or active, the ultrasound beam will be focused at a single focal point $f_1$. When the side portions 16 and 18 of the transducer element are excited the ultrasound beam will be focused at a multitude of points along a line from focal point $f_1$ to focal point $f_2$ with the lowest frequency signals being focused at focal point $f_2$. This results because transducer resonant frequency is inversely proportional to its thickness. All frequencies transmitted are present but those closest to the resonant frequency are present to a dominant extent.

Thus when the center portion 19 of the element 11 is active, it predominantly emits a high frequency ultrasound beam which is focused at focal point $f_1$. Because the side portion surface geometry of the transducer element are defined by straight lines and increase in thickness, the focal point varies along a line from focal point $f_1$ to focal point $f_2$ with the lowest frequency signal generated predominantly by the thickest part of the transducer element focused at focal point $f_2$. The focal points $f_1$ and $f_2$ are merely illustrative and are not drawn to scale. With this design, different frequency components within a single wideband excitation signal are focused at different points.

The straight segments of the surface of the transducer element make an angle $\theta$ with the elevation axis defined by the following equation:

$$\mathrm{Tan}(\theta) = \frac{w}{2 \cdot f_2},$$

where w is the width of the transducer element in the elevation direction and $f_2$ is the distant focal dimension from the center 20 of the transducer element. With a width of 14 mm and a distant focal point of 140 mm, $\theta$ equals 2.90 degrees. It is desirable to provide a smooth match between the straight segments and the center circular arc. An equation was derived using the equation for a circle and finding for what distance x from the center 20 of the element 11 the slope of the circular arc matches that of the straight segments. Using a small angle approximation, the distance x is determined by the following equation:

$$x = \frac{f_1 \cdot w}{2 \cdot f_2}$$

where $f_1$ is the focal point closest to the center 20 of the transducer element. In the presently preferred embodiment the transition from the center circular arc to the straight segments is about 2 mm from the center 20 of the transducer element 11 as shown.

Because the transducer array constructed in accordance with the present invention is capable of operating at a broad range of frequencies, the transducer is capable of receiving signals possessing center frequencies other than the transmitted center frequency. More preferably the transducer is capable of receiving reflected ultrasonic echo information in the vicinity of a harmonic frequency from the target. In particular, the ultrasonic echo information in the vicinity of a harmonic frequency will be focused at different points. For example, 3.5 MHz transmit signals may be focused at 50 mm and 3 MHz transmit signal may be focused at 100 mm. If the target has been injected with a contrast agent, because of the non-linear response of the contrast agent, a harmonic signal of 7 MHz will be reflected or returned at a range of 50 mm and a harmonic signal of 6 MHz will be reflected at a range of 100 mm.

As was previously mentioned in a preferred embodiment the receive beamformer preferably may include a dynamic receive focusing system that allows the focus of the receive beamformer to be changed at a high rate in order to follow as accurately as possible the range along the ultrasonic scan line corresponding to the currently arriving signals. Preferably, the receive beamformer includes a time-varying adjustable bandpass filter which is adjusted in real time to emphasize the frequency of the currently arriving signals. U.S. Pat. No. 4,016,750 describes a simple analog implementation for such a time-varying filter. A high-pass filter can be substituted for a bandpass filter. The body acts as a low-pass filter, and for this reason a high-pass filter may be sufficient to achieve the desired effect.

It is not necessary, however, that the receive beamformer include a time-varying filter. Reference is made to U.S. Pat.

No. 5,678,554 for further details concerning the types of filters that may be used in the receive beamformer.

It is anticipated that the transmit beamformer described in Hossack, et al. U.S. Pat. No. 5,740,128 which is hereby incorporated by reference and assigned to the assignee of the present invention can be adapted for use with this invention.

It is anticipated that the receive beamformer described in U.S. Pat. No. 5,685,308 issued Nov. 11, 1997 which is specifically incorporated herein by reference and assigned to the assignee of the present invention can be adapted for use with this invention.

Figure 4:
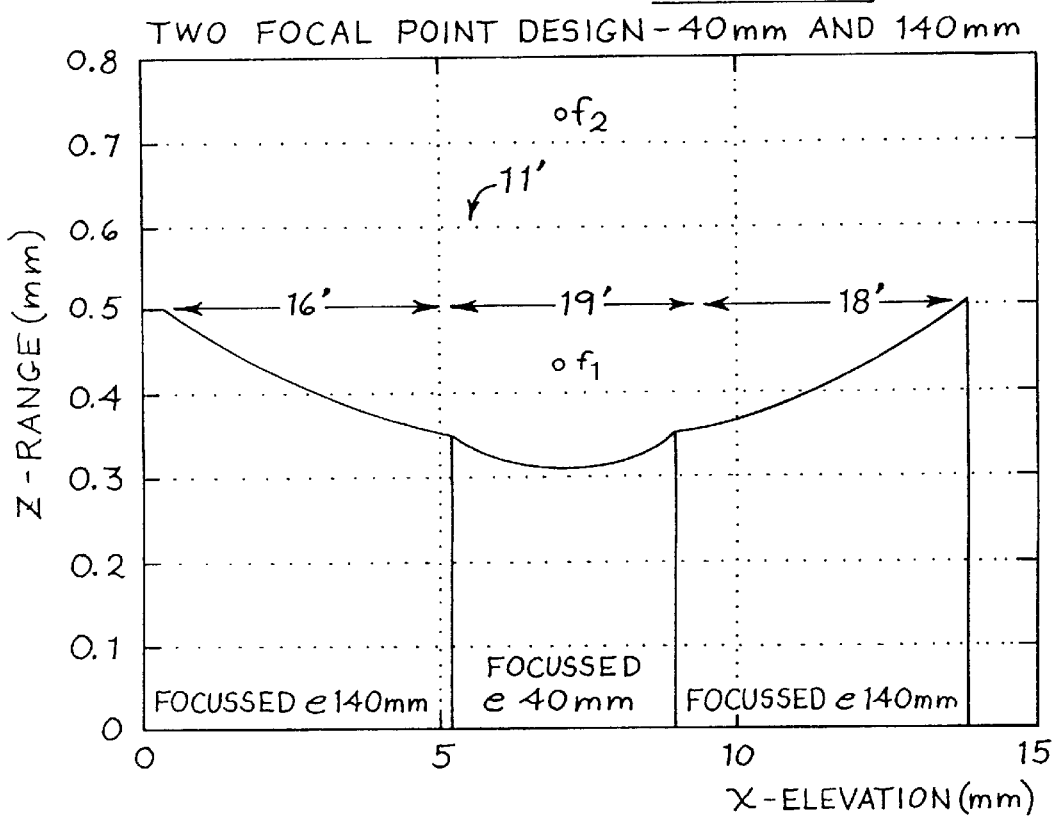
FIG. 4 is a cross-sectional profile of a transducer element according to a second preferred embodiment of the present invention.

The transducer element may have other surface geometries than that shown in FIG. 3. FIG. 4 is a cross-sectional profile of a transducer element according to a second preferred embodiment of the present invention. The axes represent the same dimensions as was shown in FIG. 3. The elevation profile or surface geometry of the transducer element 11' has a center portion 19' again formed by a circular arc that focuses the beam at a focal point $f_1$ close to the surface of the element. The side portions 16' and 18' are defined by a circular arc that has a different radius from that of the center portion 19' that focuses the beam at a second focal point $f_2$ in the far field. Unlike the transducer element of FIG. 3, the surface geometry of the transducer element 11' only allows focusing at two discrete focal points instead of a range of focal points.

Figure 5:
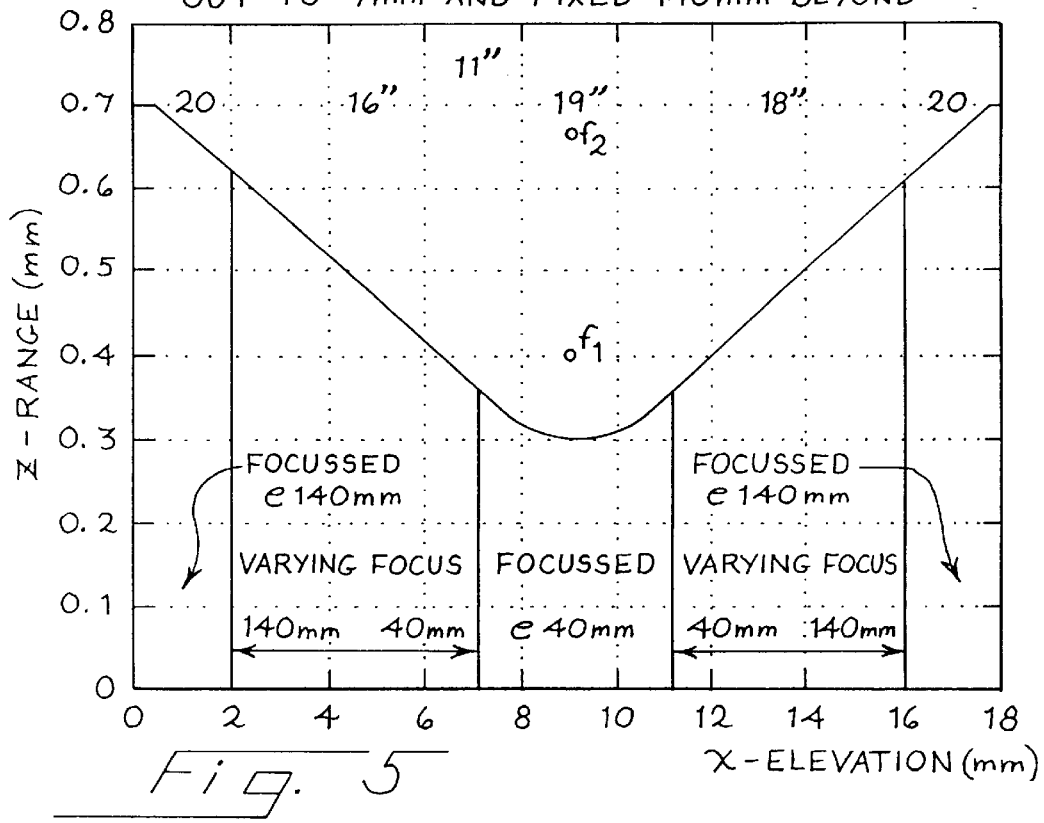
FIG. 5 is a cross-sectional profile of a transducer element according to a third preferred embodiment of the present invention.

FIG. 5 is a cross-sectional profile of a transducer element 11" according to a third preferred embodiment of the present invention. The transducer element shown in FIG. 5 combines features of both the transducer elements shown in FIGS. 3 and 4. The center portion 19" is defined by a circular arc which focuses the high frequency beams at a focal point $f_1$ close to the surface of the element. Like the transducer element shown in FIG. 3 the side portions 16" and 18" connected to the center portion 19" are straight segments that allow varying focusing from focal point $f_1$ to focal point $f_2$. The remainder of the side portions 20 are defined by a circular arc having a different radius than that which defines the center portion 19" and allows the lowest frequency signals to be focused at a focal point $f_2$.

Figure 6:
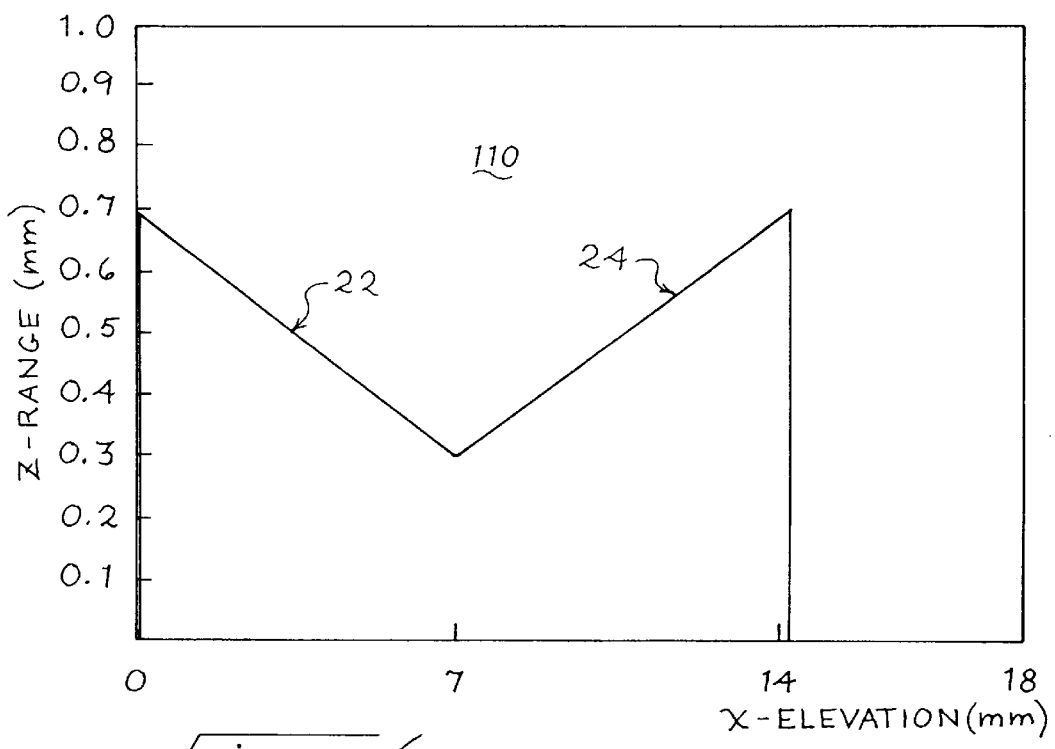
FIG. 6 is a cross-sectional profile of a transducer element according to a fourth preferred embodiment of a the present invention.

Other variations exist. FIG. 6 is a cross-sectional profile of a transducer element 11 according to a fourth preferred embodiment of the present invention. In this preferred embodiment, the active surface of each transducer element 11'" is defined by two intersecting straight surfaces 22 and 24 to define a "V" shape. In a preferred embodiment, the straight surfaces 22 and 24 have a slope of 3°.

The preferred embodiments of the transducer elements thus far described have all been of non-uniform thickness, and more preferably each transducer element has been thinnest at the center portion of the transducer element and thickest at its ends. This allows different frequency components to be focused at different focal points. Alternatively, each transducer element may have a substantially uniform thickness across the elevation direction such as the cross-sectional profiles of additional preferred embodiments shown in FIGS. 7–9. By using a uniform thickness transducer element, the same or common frequency signal is focused at different depths along a focal line extending in the range direction.

Figure 7:
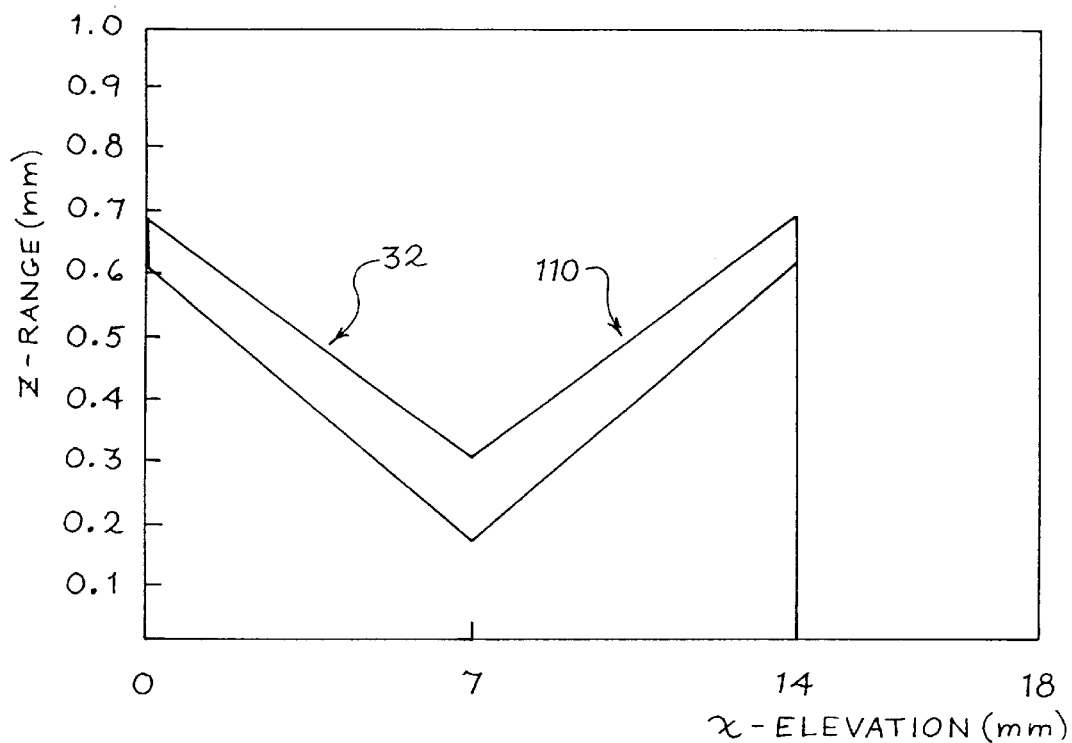
FIG. 7 is a cross-sectional profile of a transducer element according to a fifth preferred embodiment of the present invention.
Figure 8:
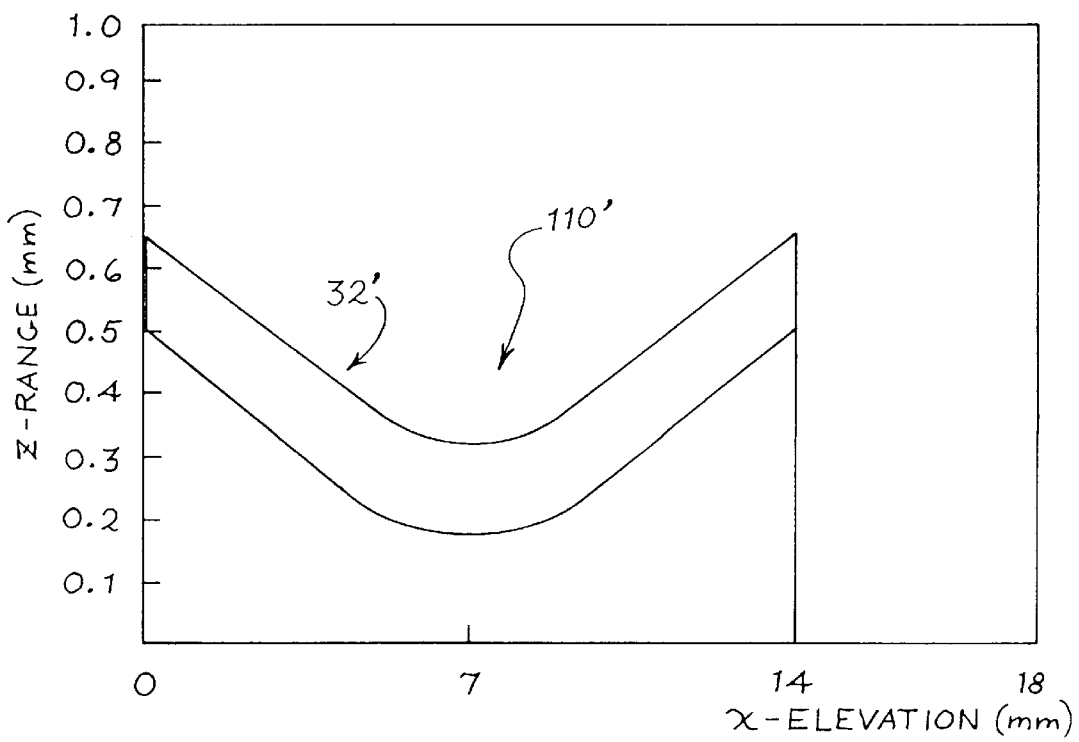
FIG. 8 is a cross-sectional profile of a transducer element according to a sixth preferred embodiment of the present invention.
Figure 9:
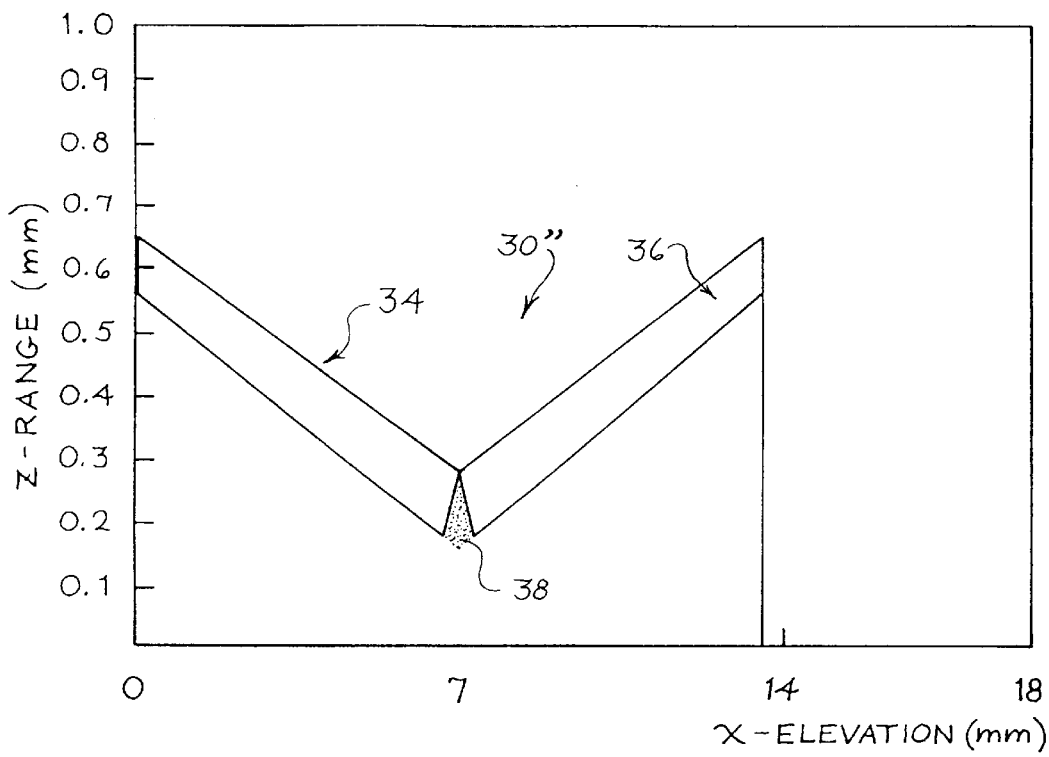
FIG. 9 is a cross-sectional profile of a transducer element according to a seventh preferred embodiment of the present invention.

FIG. 7 is a cross-sectional profile of a transducer element 110 according to a fifth preferred embodiment of the present invention. The active surface geometry 32 of the transducer element 110 shown in FIG. 7 is the same as that shown in FIG. 6. In a preferred embodiment each transducer element has a thickness measured in the z-range direction of about 0.6 mm. FIG. 8 is a cross-sectional profile of a transducer element 110' according to a sixth preferred embodiment of the present invention. The surface geometry 321 of the transducer element 110' shown in FIG. 8 is the same as that shown in FIG. 3. FIG. 9 is a cross-sectional profile of a transducer element according to a seventh preferred embodiment of the present invention. While the transducer elements shown in the previous embodiments are preferably formed from a single slab of piezoelectric material, the transducer element 110' shown in FIG. 9 is formed by two slabs of piezoelectric material 34 and 36 bonded together at 38 to form a "V" shape. Of course the embodiments shown in FIGS. 7–9 are disposed on a backing block having a complementary top surface to accommodate the shaped transducer elements.

The transducer elements may be fabricated according to the methods described in U.S. Pat. Nos. 5,415,175 and 5,438,998. In addition, one or a plurality of matching layers may be disposed on each transducer element.

Figure 10:
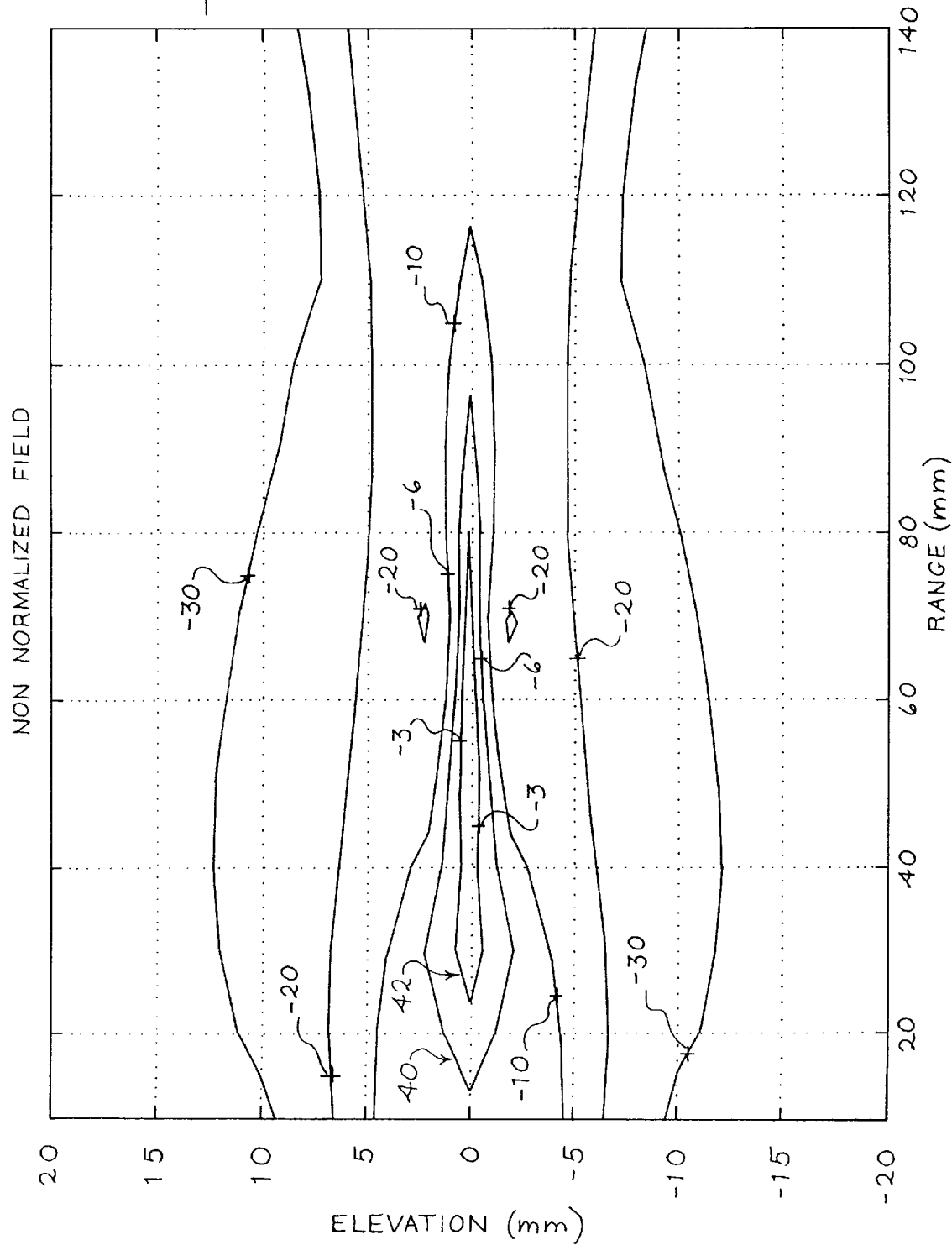
FIG. 10 is a contour plot of the intensity profile of a transducer element such as that shown in FIG. 6.
Figure 11:
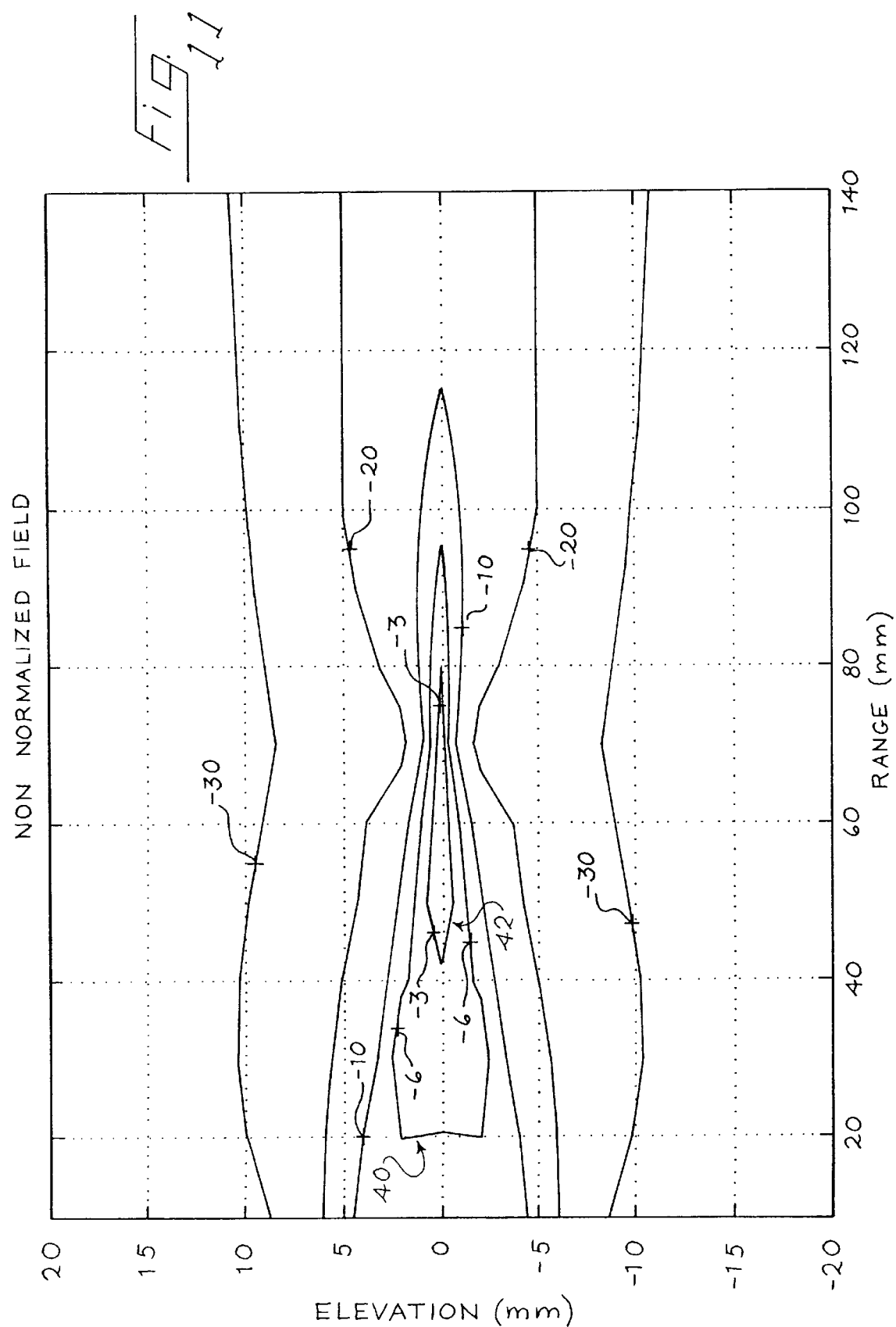
FIG. 11 is a contour plot of the intensity profile of a transducer element according to the prior art.

FIG. 10 is a contour plot of the intensity profile of a transducer element such as that shown in FIG. 6. FIG. 11 is a contour plot of the intensity profile of a transducer element having a surface geometry described by U.S. Pat. Nos. 5,415,175 and 5,438,998, i.e., a circular profile which provides only one focal point for a transmitted beam. In both graphs, range is plotted along the horizontal axis and elevation is plotted along the vertical axis and both are in division of millimeters.

It can be seen from the comparison of contour plots that an advantage of the present invention is that the region of high intensity is spread along an extended region along the axis emanating from the active transducer surface. For example if one compares the −6 dB contour line of pressure in the field shown at line 40 in the respective plots one can see that for the transducer according to the present invention that intensity level is spread over a greater range than for the prior art transducer. Line 42 in the respective graphs illustrates the −3 dB contour line of pressure. Since peak intensity is limited by government regulation, it is preferable to use a more diffuse intensity profile as a function of depth so that for the same peak intensity, high intensities in the vicinity of the peak are obtained and hence a higher cumulative non-linear effect is obtained since the non-linear effect is most significant when the intensity is highest. Further, the non-linear generation is a cumulative generation process during the propagation of the signal and hence there is benefit in rapidly increasing intensity as a function of depth, i.e., to speed the development of a non-linear second harmonic signal and to maintain the high intensity level so that second harmonic generation continues for increasing depth, and also reduces the continuous impact of attenuation, which is a function of frequency and hence affects the harmonic more than the fundamental.

Figure 12:
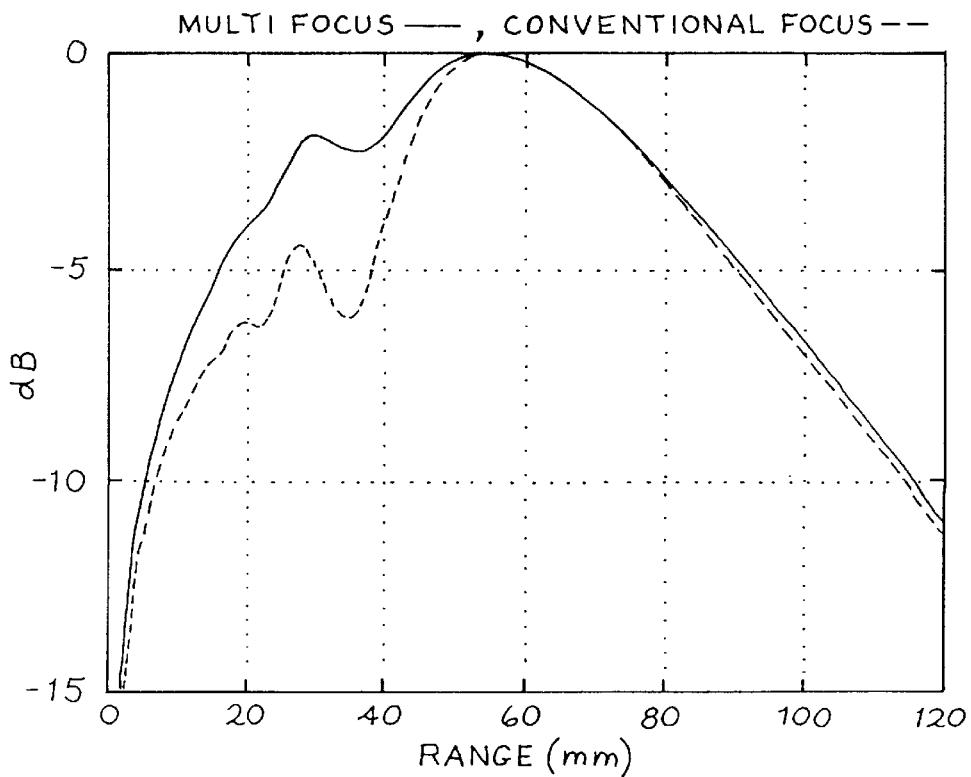
FIG. 12 is a graph comparing the intensity profiles of a transducer array according to the present invention and a transducer array according to the prior art.

FIG. 12 is a graph comparing the intensity profiles of a transducer array according to the present invention and a transducer array according to the prior art. The z-range axis has been plotted in millimeters along the horizontal axis and intensity in decibels is plotted along the vertical axis. The intensity profile for a transducer formed according to the present invention is shown in solid line and the intensity profile for a transducer formed according to the prior art is shown in dashed line. It can be appreciated that the axial beam dimension of the transducer formed according to the present invention is increased at the −3 dB and −6 dB contour lines of pressure.

Sidelobe levels, which are higher when using a focusing arrangement like that shown here are less significant since the second harmonic response is approximately related to the square of the instantaneous intensity and hence sidelobe levels are reduced with respect to main lobe levels.

The present invention, i.e., of extended focus in the elevation direction, may be used in combination with the concept of extended focus in the azimuthal direction such as that disclosed in U.S. Pat. No. 5,740,128 and U.S. Ser. No. 08/893,288 filed Jul. 15,1997, assigned to the present assignee or in combination with a conventional azimuthal focusing arrangement.

The transducer elements may be apodized to smooth out the sidelobes which may otherwise occur. Various approaches are possible, for example, by providing shaped electrodes as described in U.S. Pat. No. 4,425,525 (Smith et al.) or by degraded poling at the element ends as described in U.S. Pat. No. 4,460,841 (Smith et al.) or by providing a resistive electrode to provide a potential divider effect on the signal surface of the element as described in Hayward, G., et al., "A Thin Film Technique For Spatial Apodization of Disc-Shaped Piezoelectric Transducers," *J. Acoust. Soc. Am.*, 99(4), Pt. 1, pp. 1808–1815, April 1991.

Figure 13:
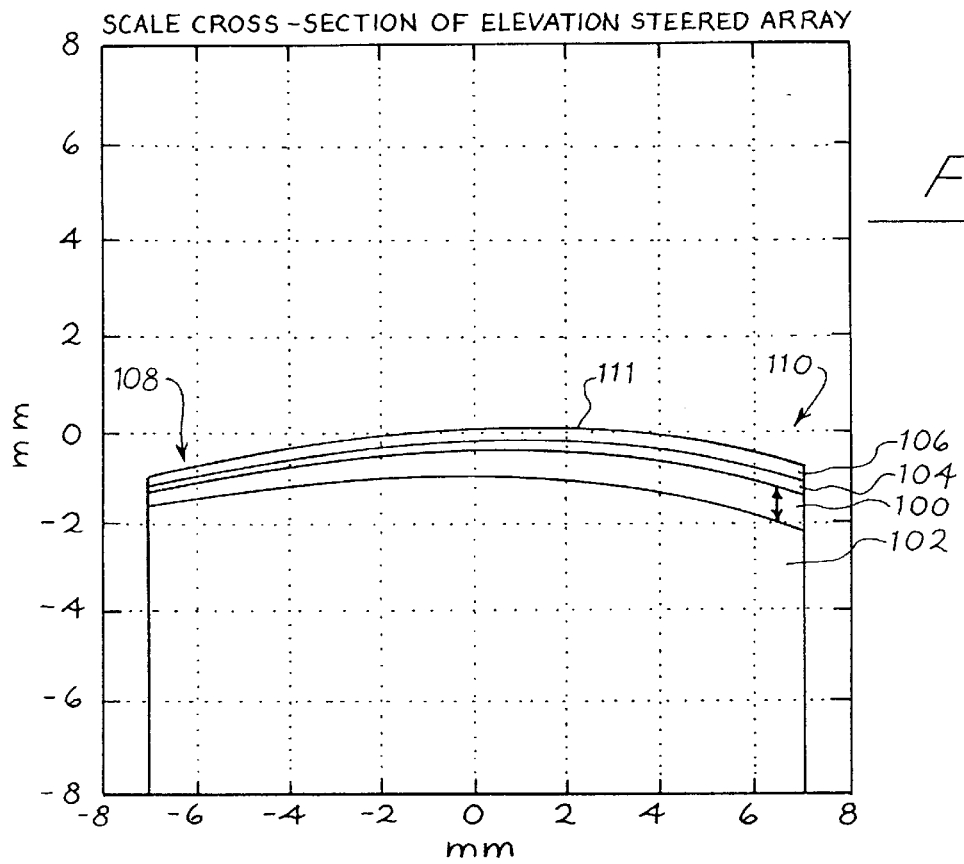
FIG. 13 is a cross-sectional profile drawn to scale of a transducer element according to a preferred embodiment of the present invention.

FIG. 13 is a cross-sectional profile drawn to scale a transducer element according to a preferred embodiment of the present invention. The transducer element 100 is disposed on a backing block 102 and two acoustic matching layers 104 and 106 are disposed on the transducers element 100. Preferably, acoustic matching layer 104 is a high impedance layer preferably formed of Dow Corning's epoxy DER 332 plus Dow Corning's curing agent DEH 24 plus a filler of 1 micron tungsten carbide and 9 micron alumina particles which are added to obtain an acoustic impedance of approximately 10.0 MRayls and acoustic matching layer 106 is a low impedance matching layer preferably formed of Dow Corning's epoxy DER 332 plus Dow Corning's curing agent DEH 24.

Figure 14:
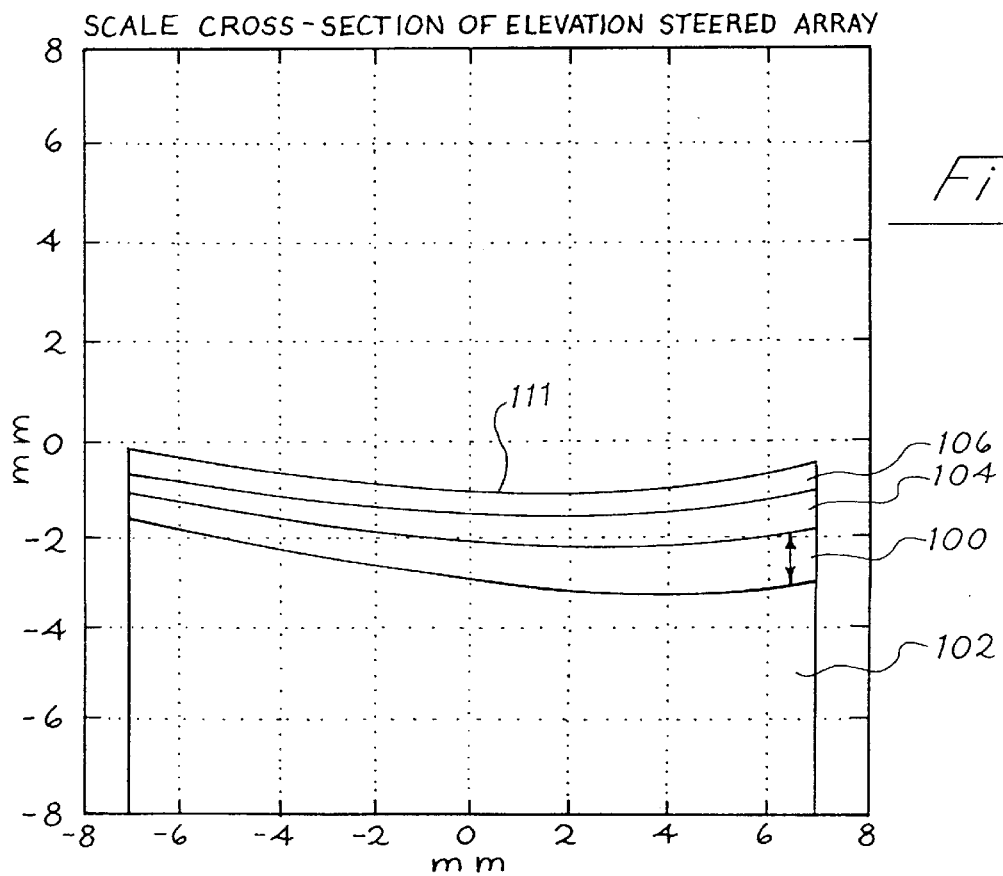
FIG. 14 is a cross-sectional profile of a transducer element according to another preferred embodiment of the present invention.

As can be seen from the profile, the array has a nonuniform thickness extending along the elevation direction so that the array is thin at end 108 and thick at the opposite end 110. While the surface 111 which will face a region of examination when the array is in use is shown convex in shape, it may alternatively be concave as shown in FIG. 14.

When the transducer is operated using a relatively low frequency with wide bandwidth a divergent beam is produced. In a preferred embodiment the radius of acoustic matching layer 106 is about 28 mm resulting in a divergent emitted ultrasound beam of about 30° wide. The dimensions of the array may be varied to obtain the maximum divergent angle desired for a particular application.

Figure 15:
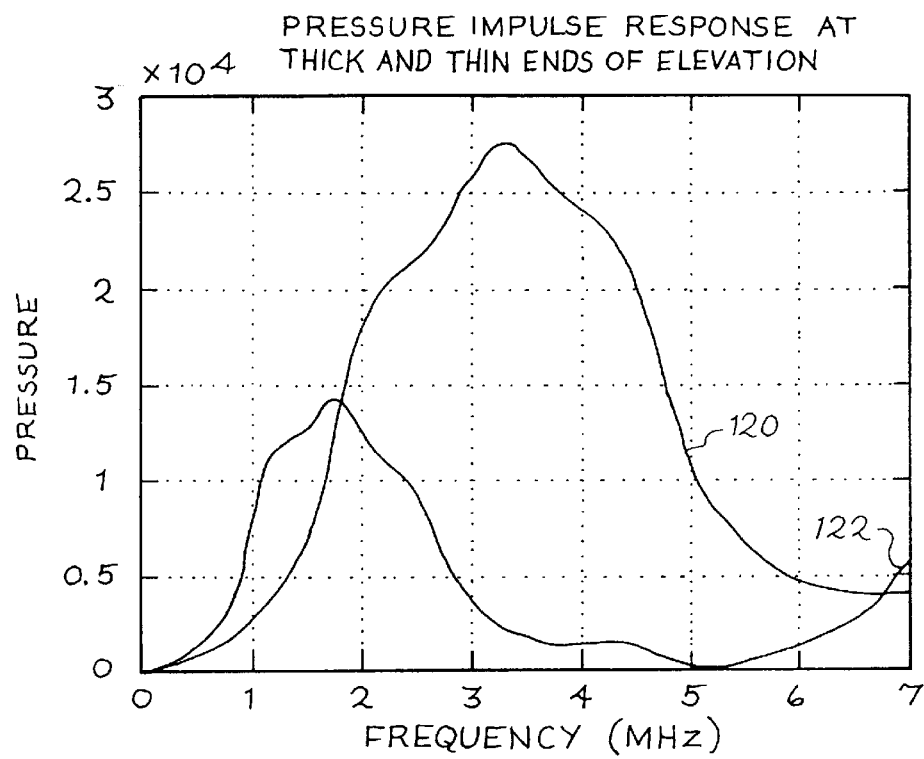
FIGS. 15–17 are graphs of the pressure impulse responses at the thick and thin ends of the transducer array shown in FIG. 13.
Figure 16:
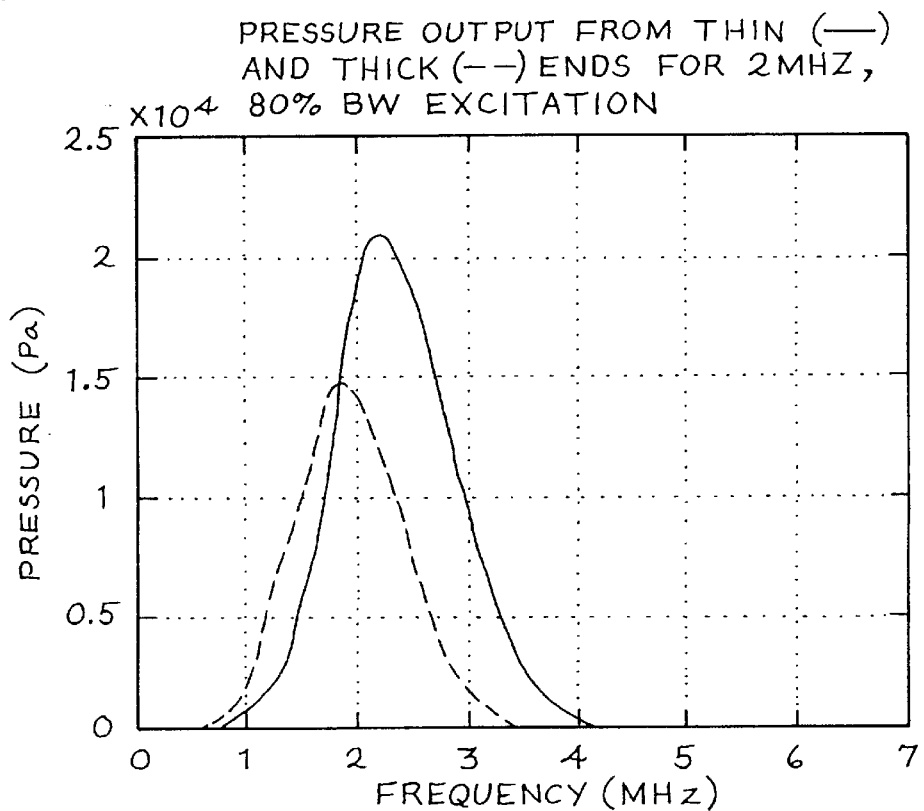
Figure 17:
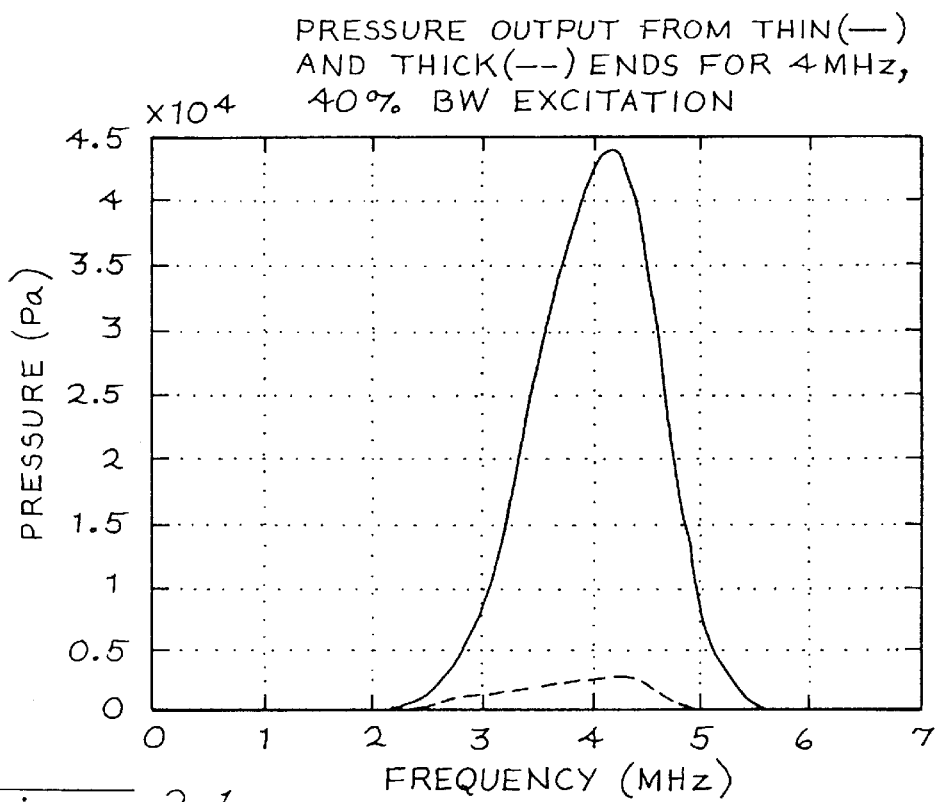

FIGS. 15–17 are graphs of the pressure impulse responses at the thick and thin ends of the transducer array shown in FIG. 13. Frequency in MegaHertz is along the horizontal axis and pressure in Pascals is along the vertical axis. The thin portion of the array has a larger pressure impulse response as shown by graph 120 than the thicker portion of the array as shown by graph 122 in FIG. 15. The array is capable of operating at about 4 MHz in the thin portion and about 2 MHz in the thick portion.

By driving the array with either high or low frequency components of controlled bandwidth and preferably possessing Gaussian envelopes, portions of the array may be selectively activated. When the transducer array is operated with a 2 MHz signal possessing a relatively wide bandwidth (80% −6 dB fractional bandwidth) a relatively uniform distribution of sensitivity across the array as shown in FIG. 16 is obtained. However, if the array is driven with a 4 MHz signal possessing a relatively narrow bandwidth (40% −6 dB fractional bandwidth), as shown in FIG. 17, then only the thinner end is active. Since the thinner end of the array is "pointing" to one side, the beam also tends to point to one side. Hence, by controlling the frequency of the excitation and/or bandwidth, or the receive bandpass filter, or any combinations of these, it is possible to control to some extent the direction and width of beam in the elevation beam.

Figure 18:
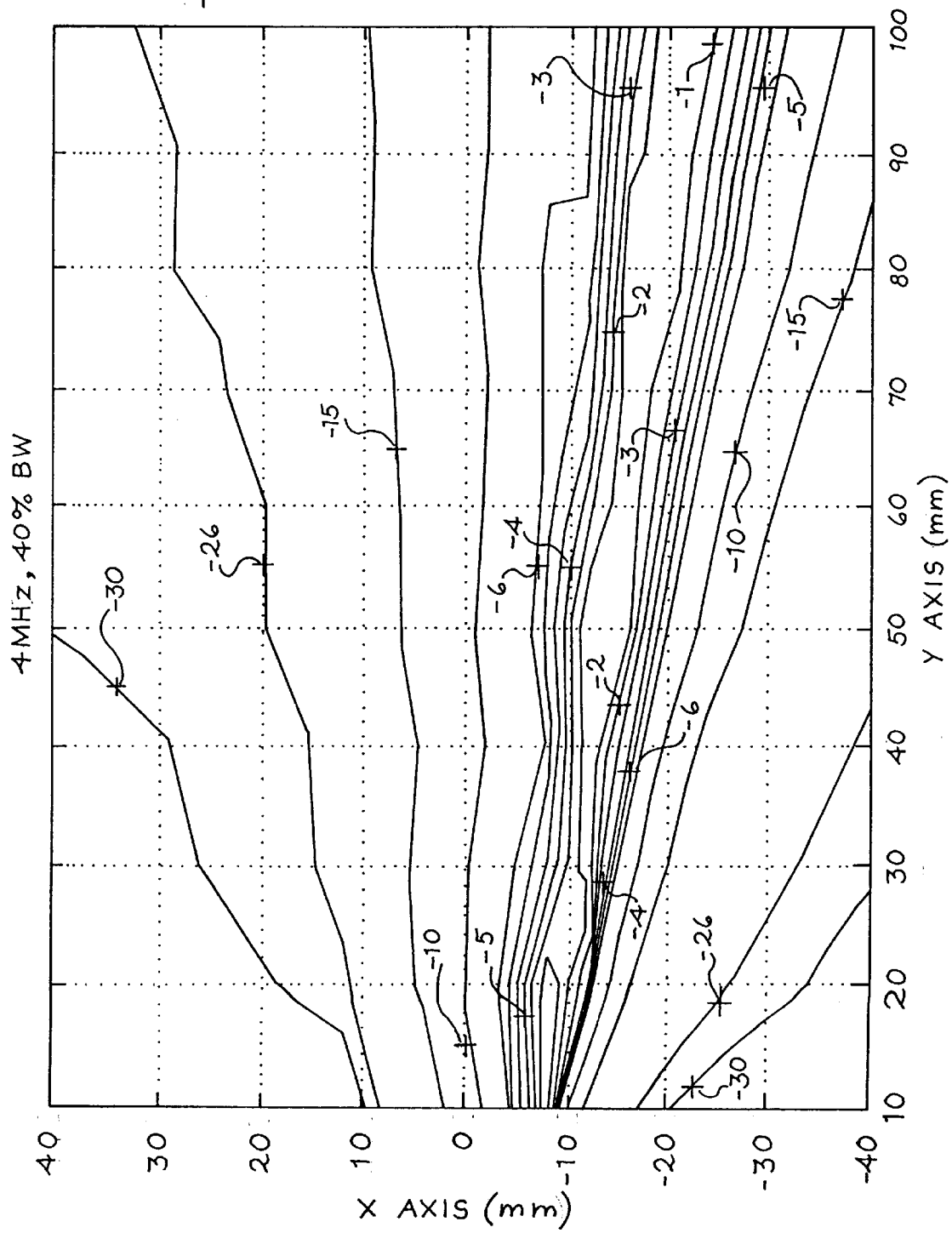
FIGS. 18 and 19 are contour plots for the transducer shown in FIG. 13.
Figure 19:
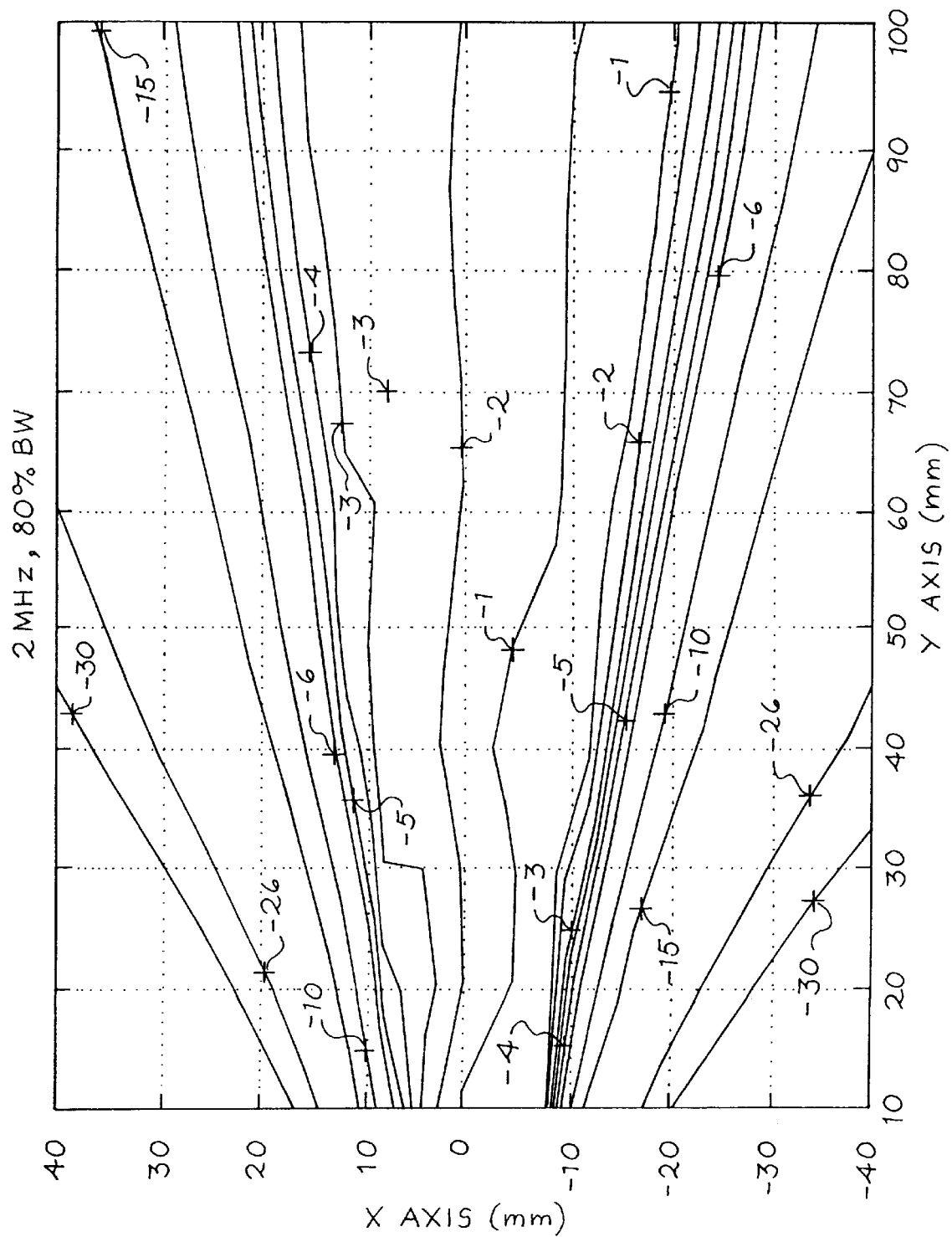

FIG. 18 is a contour plot of the beam width versus range for the transducer shown in FIG. 14 excited at 4 MHz. In a preferred embodiment the excitation pulse is generally Gaussian in shape and centered at 4 MHz. The bandwidth of the pulse is 40% of the center frequency measured at points −6 dB with respect to the peak amplitude. Such a pulse will be referred to herein as a 40% BW Gaussian pulse. As can be seen, the beam is steered off axis by approximately 11 degrees. FIG. 19 is a contour plot of the beamwidth versus range for the transducer shown in FIG. 14 excited at 2 MHz with an 80% bandwidth Gaussian pulse.

The elevation controlled beam may be used advantageously in a number of ways. First a wideband beam can be transmitted with different components separately filtered out and associated with different beam directions. The returned beams may be reconstructed in a three dimensional format. The filtering upon receipt may be simultaneous, i.e., using duplicate receive hardware for the separately filtered components, or it can be sequential by transmitting successive pulses and using different filtering on these successive pulses. If the sequential method is used, the advantage of potentially controlling the transmit frequency response may result.

When performing contrast agent harmonic imaging, in the transmit mode, the transducer array may first be excited at a dominant fundamental frequency such as 3.5 Megahertz to observe the heart or other tissues and then, in receive mode, the receive circuitry filters out all frequencies but those in the vicinity of the harmonic frequency, preferably a second harmonic frequency, in order to make the contrast agent more clearly visible relative to the tissue. In addition, the present invention can be used for tissue harmonic imaging when no contrast agent is used. When observing the fundamental frequency, filters, i.e., electrical filters, centered around the fundamental frequency may be used. When observing a harmonic signal, filters centered around the harmonic frequency may be used. For example U.S. Pat. No. 5,696,737 which is hereby incorporated herein by reference and assigned to the present assignee discloses an ultrasonic imaging system and method that includes a transmit waveform generator coupled to a transducer array that causes the transducer array to emit a signal having a bandwidth controlled such that substantially no second harmonic energy is transmitted and it discloses a receiver coupled to the transducer array which is selectively responsive to second harmonic echo information. A contrast agent such as FS069 available from Molecular Biosystems, Inc. of San Diego, California may be used. The transmit generator may include a low-pass filter to control the bandwidth of the emitted signal. The receiver may include a time-varying frequency filter responsive to second harmonic echo information. For further details reference is made to U.S. Pat. No. 5,696,737. Although the transducer may be set in the receive mode at a harmonic frequency as described above, the transducer array may be capable of transmitting and receiving at the fundamental frequency and a harmonic frequency. As used herein, "harmonic" is intended broadly to include subharmonics and fractional harmonic energy (e.g., ½ or ⅔ of the fundamental), as well as higher harmonics (e.g., 2 or 3 times the fundamental).

The ultrasound transducer according to the present invention may be used selectively for fundamental imaging, harmonic imaging or a combination thereof. For example, U.S. Ser. Nos. 08/904,829 and 08/838,920, which are assigned to the present assignee and hereby incorporated by reference disclose such methods. With user input (not shown) such as a keyboard with various dedicated keys and a track ball, the user selects the type of image or images for display. The images are based on various processing modes known in the art. For example, a B-mode image, a M-mode image, a color M-mode image, a color Doppler velocity image (CDV), a color Doppler energy image (CDE), a Doppler Tissue image (DTI), a CW spectral Doppler image, or a PW spectral Doppler image may be selected.

Figure 20:
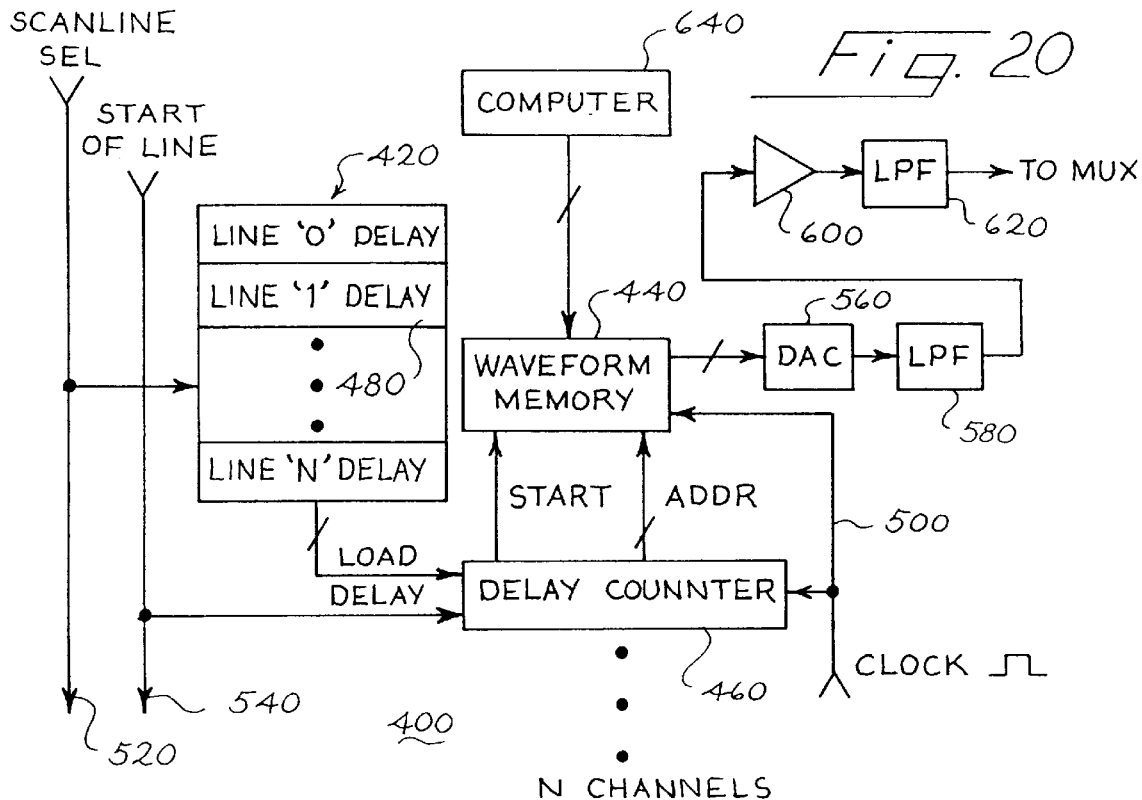
FIG. 20 shows a block diagram of a first preferred embodiment of a transmit beamformer of FIG. 1.

FIG. 20 shows a block diagram of a first preferred embodiment 400 of the transmit beamformer that may be used in the transmit circuitry of FIG. 1. As shown in FIG. 20, the transmit beamformer 400 includes N channels, one for each of the transducer elements 11 of the transducer array 14 (FIG. 2). Each channel includes a delay memory 420, a waveform memory 440, and a delay counter 460. The delay memory 420 includes 256 words 480, one for each possible steering angle or ultrasound transmit scan line. Each word 480 of the delay memory 420 is set equal to a negative number equal to the number of clock cycles on the clock signal line 500 that elapse between a start of line signal on line 540 and the first non-zero value of the associated waveform. For simplicity, it is assumed that zero is defined as a word 48 having the most significant bit equal to one and all other bits equal to zero. Hence, the most significant bit becomes an enable signal for the waveform memory 440.

The waveform memory 440 in this embodiment stores a single waveform in digital form, which is used for all transmit scan lines. The waveform memory 440 can include for example 64 or 128 successive 8 bit words. The magnitude of each 8 bit word corresponds to the voltage amplitude at the respective position in the waveform. When the waveform memory 440 is read with a 40 MHz clock on the line 500, the resulting sequence of digital values defines a waveform approximately 1.6 to 3.2 microseconds in duration.

The delay memory 420 is not required, but it reduces memory requirements for the waveform memory 440. This is because the delay memory 420 eliminates the need to store a large number of leading zeros when the ultrasound line is steered at a large angle.

In use, each channel responds to a scan line selection signal on line 520 by loading the word 480 for the selected scan line into the delay counter 460. The delay counter 460 responds to a start of scan line signal on line 540 by incrementing the stored value with each cycle of the 40 MHz clock on line 500. When the counter 460 increments to zero, it enables the waveform memory 440. Subsequently generated values of the counter 460 (incrementing now from zero upwards) become address values for the waveform memory 440. As each word of the waveform memory 440 is addressed, the corresponding 8 bit word is read and applied to a digital to analog converter 560.

The analog output signal of the converter 560 is passed through a low pass filter such as a Bessel filter 580 to reduce sampling effects and then to an amplifier 600. The output of the amplifier 600 can be passed through an additional low pass filter 620 to improve harmonic rejection. The output of the low pass filter 620 is the transmit waveform discussed above that is applied to the respective transducer via a multiplexer.(not shown). The low pass filters 580, 620 preferably provide a sharp cut-off with a low stop band level in order substantially to eliminate ultrasonic energy in the transmitted pulse at the harmonic frequency.

The transmit beamformer 400 utilizes values for the waveforms stored in the waveform memory 440 and the delays stored in the delay memory 420 that enhance insonification of the contrast agent in the subject.

Figure 21:
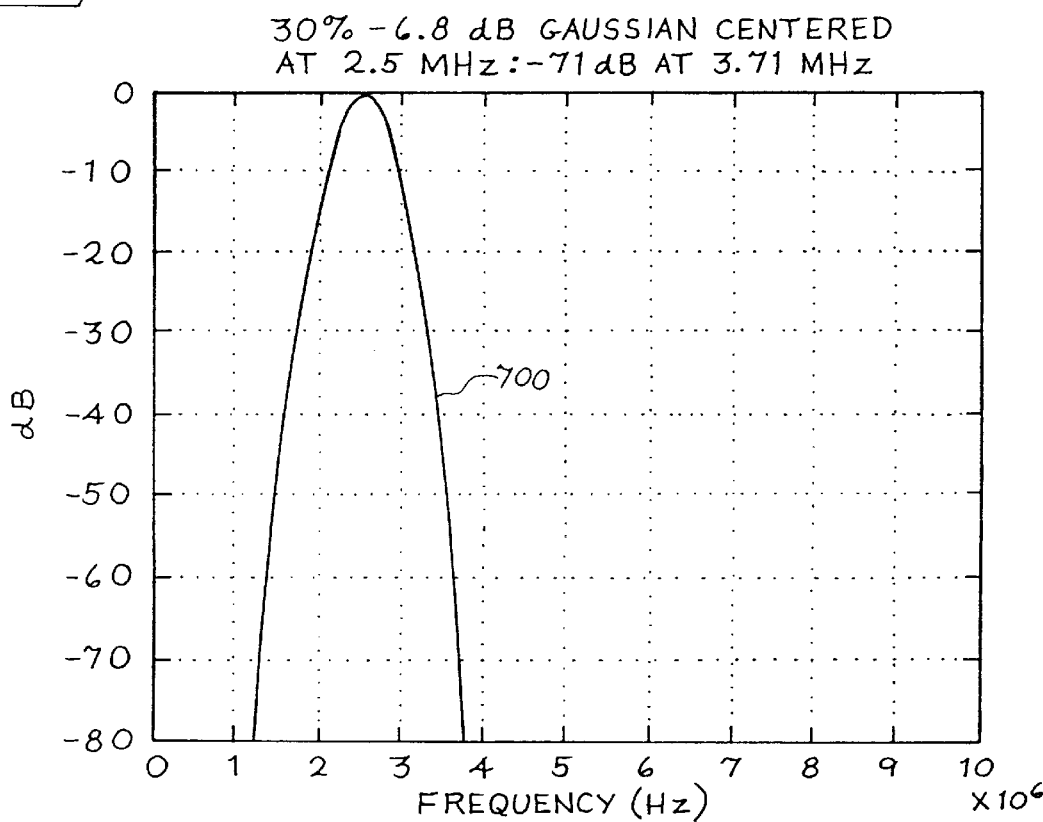
FIG. 21 shows the frequency spectrum of one suitable pulse which is generally Gaussian in shape.

The waveform stored in the waveform memory 440 is shaped to suppress ultrasonic energy in a wide pass band centered at the harmonic frequency. For example, the spectrum of the desired pulse can be designed on a computer 640. FIG. 21 shows the frequency spectrum of one suitable pulse 700 which is centered at the fundamental frequency of 2.5 MHz and is generally Gaussian in shape. The particular Gaussian shape shown in FIG. 20 has an amplitude reduced by 71 dB at 3.71 MHz. The bandwidth of the pulse 700 is 30% of the center frequency, measured at points −6.8 dB with respect to the peak amplitude. Such a pulse will be referred to herein as a 30% BW Gaussian pulse. Note that the pulse 700 has substantially no energy at 5 MHz, the first harmonic of the fundamental frequency. This invention is not limited to use with Gaussian pulses, and a wide range of spectra can be used.

Figure 22:
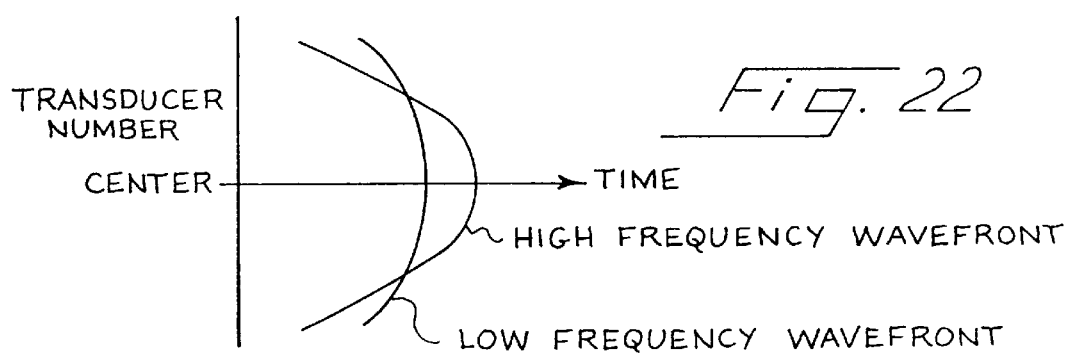
FIGS. 22 and 23 are graphs showing the high end low frequency wavefronts in two alternate sets of transmit waveforms.
Figure 23:
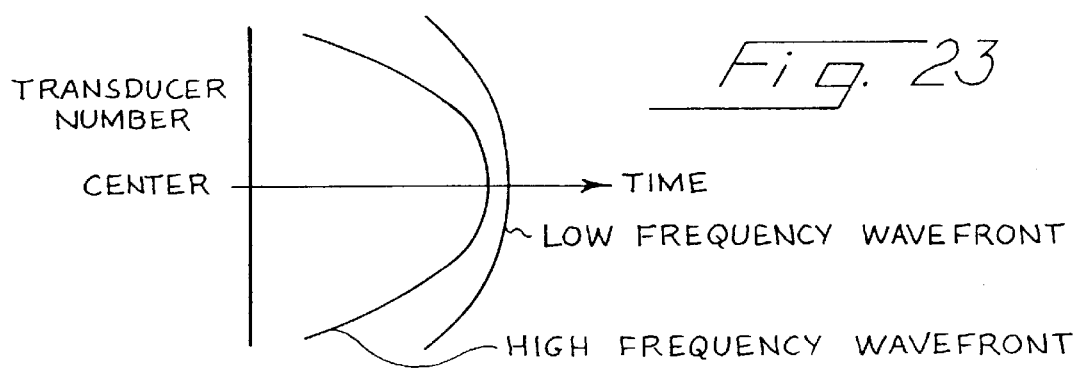

In certain applications it is desirable to produce temporarily long waveforms. Coded waveforms of the type described by M. O'Donnell in IEEE Trans. UFFC Vol. 39, No. 3, pp. 341–351 may also be used with this invention. These waveforms, which are essentially 'chirp' waveforms, have the advantage of higher signal to noise since they increase pulse energy without increasing peak power and hence take advantage of the fact that regulatory limits on peak acoustic power are more burdensome than the limits on peak acoustic energy in this application. (Signal to noise is related more to signal energy than signal power). Since the different frequency components are focused to different points, the nature of the focused waveform will vary with range. Nevertheless, by filtering to a reduced bandwidth (e.g., 30% −6 dB fractional bandwidth), the resultant waveform will contain well focused components. Another feature of 'chip'-like waveforms is that if the low frequencies occur earlier than the high frequency components, the total temporal spread in the waveforms applied to the end elements may be reduced. FIG. 22 illustrates the high and low frequency components in such a case. Note that the total delay from the start to finish of the transmit waveforms is reduced in FIG. 22 as compared to FIG. 23, which shows the alternate relationship.

All of the harmonic imaging techniques described above can be used in both tissue and contrast agent harmonic imaging modes. In the tissue harmonic imaging mode no additional contrast agent is added to the target, and only the native non-linear characteristics of the tissue are relied on to create the ultrasonic image. Medical ultrasound imaging is typically conducted in a discrete imaging session for a given subject at a given time. For example, an imaging session can be limited to an ultrasound patient examination of a given tissue of interest over a period of ¼ to 1 hour, though other durations are possible. In this case no additional contrast agent is introduced into the tissue at any time during the imaging session. In the contrast agent harmonic imaging mode, any one of a number of well known contrast agents such as those described above can be added to the target in order to enhance the non-linear harmonic response of the tissue. For this reason, it should be understood that the introduction of an added contrast agent into the tissue being imaged is not implied in any of the following claims unless such added contrast agent is expressly recited. It is to be understood that the forms of the invention as described herewith are to be taken as preferred examples and that various changes in the shape, size, and arrangement of parts may be resorted to, without departing from the spirit of the invention or scope of the claims.

What is claimed is:

1. A method for ultrasonically imaging a target during an imaging session, said method comprising the following steps:
   (a) transmitting ultrasonic energy at a fundamental frequency into the target from a plurality of transducer elements wherein each transducer element has a non-planar surface and a shape that focuses different frequency components at different focal points along a focal line; and
   (b) selectively receiving ultrasonic echo information in the vicinity of a harmonic frequency from the target while filtering out ultrasonic echo information at the fundamental frequency.

2. The method according to claim 1 wherein the transmitting step (a) further comprises the step of controlling bandwidth of the transmitted ultrasonic energy to substantially prevent transmission of ultrasonic energy at a second harmonic frequency of the fundamental frequency.

3. The method according to claim 1 wherein the receiving step (b) further comprises the step of using a time-varying frequency filter to filter out ultrasonic echo information at the fundamental frequency.

4. The method of claim 1 wherein said target is free of contrast agent throughout the entire imaging session.

5. The method of claim 1 further comprising the step of injecting a contrast agent into the target either before or during the imaging session.

6. The method of claim 1 wherein the transmitting step (a) further comprises the step of phasing a plurality of transmit waveforms.

7. The method of claim 6 wherein the plurality of transmit waveforms comprises a central transmit waveform associated with a central one of the transducer elements, wherein the central transmit waveform comprises a lower frequency component and a higher frequency component, and wherein the lower frequency component of the central transmit waveform occurs earlier in time than the higher frequency component of the central transmit waveform.

8. An ultrasonic imaging system comprising:
   an ultrasonic transducer array comprising a plurality of transducer elements wherein each element has a non-planar surface in an elevation direction, and each transducer has a shape that focuses different frequency components at different focal points along a focal line;
   transmit circuitry coupled to the transducer array, said transmit circuitry operative to transmit energy at a fundamental frequency; and
   receive circuitry coupled to the transducer array, said receive circuitry operative to selectively receive ultrasonic echo information in the vicinity of a harmonic frequency from the target while filtering out ultrasonic echo information at the fundamental frequency.

9. The ultrasonic imaging system of claim 8 wherein the receive circuitry comprises a time-varying frequency filter responsive to second harmonic echo information.

10. The ultrasonic imaging system of claim 8 wherein the transmit circuitry comprises a filter for controlling bandwidth of the transmitted ultrasonic energy to substantially prevent transmission of ultrasonic energy at a second harmonic frequency of the fundamental frequency.

11. The system of claim 8 wherein each of the plurality of transducer elements has a non-uniform thickness measured in a range direction.

12. The system of claim 8 wherein each of the transducer elements has a center portion defined along an elevation direction and side portions on opposite sides of the center portion defined along an elevation direction wherein the center portion has a shape different from the side portions.

13. The system of claim 12 wherein the center portion has a first radius of curvature and the side portions have a second radius of curvature, the first radius of curvature being different from the second radius of curvature.

14. The system of claim 12 wherein the center portion and side portions define an ellipse.

15. The system of claim 12 wherein the side portions are formed by straight lines and the center portion is formed by a circle.

16. The system of claim 15 wherein the side portions form an angle $\theta$ with a horizontal axis where $\theta$ is defined by the equation $$\theta = \tan^{-1}\left(\frac{w}{(2)(f_2)}\right),$$

where w is the width of the transducer element in the elevation direction and $f_2$ equals the distance of the furthest focal point from the surface of the transducer element.

17. The system of claim 15 wherein the side portions begin a distance X from the center of the curved portion where X is defined by the equation $$x = \frac{(f_1)(w)}{(2)(f_2)},$$

where $f_1$ equals the distance of the closest focal point from the surface of the transducer element and $f_2$ equals the distance of the furthest focal point from the surface of the transducer element.

18. The system of claim 8 further comprising at least one acoustic matching layer disposed on the surface facing the region of examination of each transducer element.

19. The system of claim 8 wherein each of the transducer elements has a shape that can focus different frequency components at two discrete focal points.

20. The system of claim 8 wherein each of the transducer elements has a shape that can focus a beam along a line of focal points.

21. The system according to claim 20 wherein the line of focal points is perpendicular to an elevation axis.

22. An ultrasonic imaging system according to claim 8 further comprising a time-varying filter coupled to the receive circuitry wherein the time-varying filter varies its passband characteristics to receive different harmonics for different transmitted fundamental frequency signals.

23. A method for ultrasonically imaging a target during an imaging session, said method comprising the steps of:
   (a) transmitting ultrasonic energy at a fundamental frequency into the target by a transducer element wherein the transducer element has a shape that focuses different fundamental frequency components at different focal points; and
   (b) receiving ultrasonic echo information in the vicinity of a harmonic frequency from the target while filtering out ultrasonic echo information at the fundamental frequency;
   (c) generating an image display from ultrasonic echo information of the harmonic frequency.

24. The method according to claim 23 wherein the transmitting step (a) further comprises the step of controlling bandwidth of the transmitted ultrasonic energy at a second harmonic frequency of the fundamental frequency.

25. The method according to claim 23 wherein the receiving step (b) further comprises the step of using a time-varying frequency filter to filter out ultrasonic echo information at the fundamental frequency.

26. An ultrasonic imaging system according to claim 8 wherein the transmit circuitry transmits an excitation signal having a Gaussian spectrum.

27. A method for ultrasonically imaging a target during an imaging session, said method comprising the following steps:
   (a) transmitting ultrasonic energy at a fundamental frequency into the target from a plurality of transducer elements wherein each transducer element has a non-planar surface and a shape that focuses common frequency components at different focal points along a focal line; and
   (b) selectively receiving ultrasonic echo information in the vicinity of a harmonic frequency from a target while filtering out ultrasonic echo information at the fundamental frequency.

28. The method of claim 27 wherein the transmitting step (a) further comprises the step of controlling bandwidth of the transmitted ultrasonic energy at a second harmonic frequency of the fundamental frequency.

29. The method according to claim 27 wherein the receiving step (b) further comprises the step of using a time-varying frequency filter to filter out ultrasonic echo information at the fundamental frequency.

30. The method of claim 27 wherein said target is free of contrast agent throughout the entire imaging session.

31. The method of claim 27 further comprising the step of injecting a contrast agent into the target either before or during the imaging session.

32. The method of claim 27 wherein the transmitting step (a) further comprises the step of phasing a plurality of transmit waveforms.

33. The method of claim 32 wherein the plurality of transmit waveforms comprises a central transmit waveform associated with a central one of the transducers, wherein the central transmit waveform comprises a lower frequency component and a higher frequency component, and wherein the lower frequency component of the central transmit waveform occurs earlier in time than the higher frequency component of the central transmit waveform.

34. An ultrasonic imaging system comprising:
   an ultrasonic transducer array comprising a plurality of transducer elements wherein each element has a non-planar surface in an elevation direction, and each transducer has a shape that focuses common frequency components at different focal points along a focal line;
   transmit circuitry coupled to the transducer array, said transmit circuitry operative to transmit energy at a fundamental frequency; and
   receive circuitry coupled to the transducer array, said receive circuitry operative to selectively receive ultrasonic echo information in the vicinity of a harmonic frequency from the target while filtering out ultrasonic echo information at the fundamental frequency.

35. The system of claim 34 wherein each of the plurality of transducer elements has a uniform thickness measured in a range direction.

36. The system of claim 34 wherein each of the plurality of transducer elements has a non-uniform thickness measured in range direction.

37. The system of claim 34 further comprising at least one acoustic matching layer disposed on the surface facing the region of examination of each transducer element.

38. An ultrasonic imaging system according to claim 34 wherein the transmit circuitry transmits an excitation signal having a Gaussian spectrum.

39. A method for ultrasonically imaging a target during an imaging session, said method comprising the steps of:
   (a) transmitting ultrasonic energy at a fundamental frequency into the target by a transducer array wherein the transducer array has a shape that focuses common fundamental frequency components at different focal points; and
   (b) selectively filtering out ultrasonic echo information at the transmitted fundamental frequency;
   (c) generating an image display from second harmonic echo information.

40. An ultrasonic imaging system comprising:
   an ultrasonic transducer array comprising a plurality of transducer elements, each of the transducer elements having a thickness that varies in the elevation direction from a first end to a second end of the transducer element, wherein the transducer element is thinnest at the first end and thickest at the second end;
   transmit circuitry coupled to the transducer array, said transmit circuitry operative to transmit energy at a fundamental frequency; and
   receive circuitry coupled to the transducer array, said receive circuitry operative to selectively receive ultrasonic echo information in the vicinity of a harmonic frequency from the target while filtering out ultrasonic echo information at the fundamental frequency.

41. An ultrasonic imaging system according to claim 40 wherein each of said transducer elements has a non-planar surface facing a region of examination when the transducer array is in use.

42. An ultrasonic imaging system according to claim 41 wherein said non-planar surface is convex.

43. An ultrasonic imaging system according to claim 41 wherein said non-planar surface is concave.

* * * * *

UNITED STATES PATENT AND TRADEMARK OFFICE
CERTIFICATE OF CORRECTION

PATENT NO.    : 6,027,448
DATED         : February 22, 2000
INVENTOR(S)   : John A. Hossack et al.

It is certified that error appears in the above-identified patent and that said Letters Patent is hereby corrected as shown below:

Title page,
Page 2, line 38, delete "Ultrasund" and substitute -- Ultrasound -- in its place.

Column 3,
Line 54, delete "a" before "the".

Column 5,
Line 17, delete "togas" and substitute -- to as -- in its place.

Column 12,
Line 37, delete "chip" and substitute -- chirp -- in its place.

Signed and Sealed this

Twenty-sixth Day of February, 2002

Attest:

JAMES E. ROGAN
*Attesting Officer*         *Director of the United States Patent and Trademark Office*